US009963744B2

(12) United States Patent
Im et al.

(10) Patent No.: US 9,963,744 B2

(45) Date of Patent: May 8, 2018

(54) COMPOSITION FOR PROMOTING CHONDROCYTE DIFFERENTIATION OR TREATING CARTILAGE DISEASES, CONTAINING KLF10 EXPRESSION INHIBITOR, AND METHOD FOR PROMOTING CARTILAGE DIFFERENTIATION BY USING SAME

(71) Applicants: DONGUK UNIVERSITY INDUSTRY-ACADEMIC COOPERATION FOUNDATION, Seoul (KR); KOREA HEALTH INDUSTRY DEVELOPMENT INSTITUTE (KHIDI), Chungcheongbuk-do (KR)

(72) Inventors: Gun-Il Im, Anyang-si (KR); Jong-Min Lee, Goyang-si (KR)

(73) Assignee: DONGGUK UNIVERSITY INDUSTRY—ACADEMIC COOPERATION FOUNDATION, Seoul (KR)

( * ) Notice: Subject to any disclaimer, the term of this patent is extended or adjusted under 35 U.S.C. 154(b) by 0 days. days.

(21) Appl. No.: 15/108,525

(22) PCT Filed: Dec. 30, 2014

(86) PCT No.: PCT/KR2014/013006

§ 371 (c)(1),
(2) Date: Jun. 27, 2016

(87) PCT Pub. No.: WO2015/102351

PCT Pub. Date: Jul. 9, 2015

(65) Prior Publication Data

US 2017/0016003 A1 Jan. 19, 2017

(30) Foreign Application Priority Data

Dec. 31, 2013 (KR) ........................ 10-2013-0168736
Dec. 29, 2014 (KR) ........................ 10-2014-0191592

(51) Int. Cl.

| | |
|---|---|
| ***A61K 31/70*** | (2006.01) |
| ***C07H 21/02*** | (2006.01) |
| ***C07H 21/04*** | (2006.01) |
| ***C12Q 1/68*** | (2018.01) |
| ***C12N 5/077*** | (2010.01) |
| ***C12N 15/113*** | (2010.01) |
| *C12N 5/00* | (2006.01) |

(52) U.S. Cl.

CPC ......... *C12Q 1/6883* (2013.01); *C12N 5/0655* (2013.01); *C12N 15/113* (2013.01); *C12N 2310/14* (2013.01); *C12N 2310/141* (2013.01); *C12N 2310/531* (2013.01); *C12N 2501/60* (2013.01); *C12N 2501/65* (2013.01); *C12N 2506/1353* (2013.01); *C12N 2510/00* (2013.01); *C12Q 2600/136* (2013.01); *C12Q 2600/158* (2013.01); *C12Q 2600/178* (2013.01)

(58) Field of Classification Search

None

See application file for complete search history.

(56) References Cited

FOREIGN PATENT DOCUMENTS

KR 10-2009-0069013 A 6/2009

OTHER PUBLICATIONS

B. Hopwood et al., "Gene expression profile of the bone microenvironment in human fragility fracture bone", Bone, vol. 44, pp. 87-101 (Sep. 10, 2009).

Gunil Im et al., "Overexpression of PTHrP-related miRNA in Human Bone Marrow Derived Stem Cells Emhances Chondrogenesis and inhibits Hypertrophy",ASBMR (American Society for Bone and Mineral Research) Annual Meeting (2012).

Ying-Jie Guan et al., "MiR-365: a mechanosensitive microRNA stimulates chondrocyte differentiation through targeting histone deacetylase 4", The FASEB Journal, vol. 25, pp. 4457-4466 (Dec. 2011).

International Search Report dated Mar. 27, 2015.

*Primary Examiner* — Sean McGarry

(74) *Attorney, Agent, or Firm* — Lucas & Mercanti, LLP

(57) ABSTRACT

The present invention relates to a Krueppel-like factor 10 (KLF10) gene expression inhibitor promoting cartilage differentiation, and more specifically, to: a composition for promoting chondrocyte differentiation or treating cartilage diseases, containing a KLF10 gene expression inhibitor promoting cartilage differentiation and inhibiting the hypertrophy and dedifferentiation of chondrocytes; a cell therapeutic agent containing the composition; a method for promoting cartilage differentiation in bone marrow stem cells, comprising a step of expressing the composition in bone marrow stem cells; and a method for screening a chondrocyte differentiation promoter or a chondrocyte therapeutic agent. The present invention first examined the generation inhibition mechanism of indian hedgehog (IHH) protein of which the molecular biological mechanism has not yet been clearly examined, and ascertained that chondrocyte differentiation is promoted and chondrocyte hypertrophy is inhibited when chondrocyte differentiation is induced by expressing the KLF10 expression inhibitor in bone marrow stem cells. Therefore, the present invention has an advantage of enabling the use of bone marrow stem cells, which express a KLF10 expression inhibitor, as a chondrocyte therapeutic agent.

14 Claims, 9 Drawing Sheets

FIG. 1A
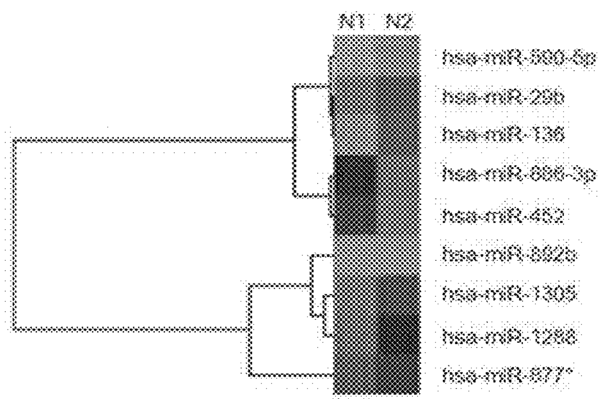
FIG.1B
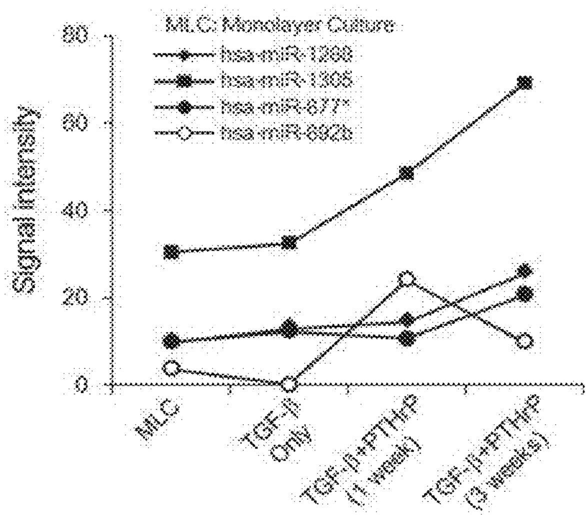
FIG.1C
| Symbol | Mature Sequence | Chromosomal Location | Assession No. |
| --- | --- | --- | --- |
| hsa-miR-1268-3P | 5P-GCAGAUCAGGACUGUAACUCACC<br>3P-UGGACUGCCCUGAUCUGGAGA<br>(SEQ ID NO: 5) | chr17:16185370-16185392 | MI0006432 |
| hsa-miR-1305 | UUUUCAACUCUAAUGGGAGAGA<br>(SEQ ID NO: 7) | chr4:183090500-183090517 | MI0006372 |
| hsa-miR-877* | UCCUCUUCUCCCUCCUCCCAG<br>(SEQ ID NO: 8) | chr6:030552182-030552194 | MI0005561 |
| hsa-miR-892b | CACUGGCUCCUUUCUGGGUAGA<br>(SEQ ID NO: 4) | chrX: 145078716-145078792 | MI0005538 |

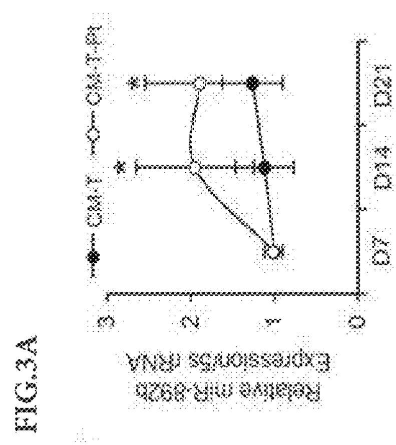
FIG.3A
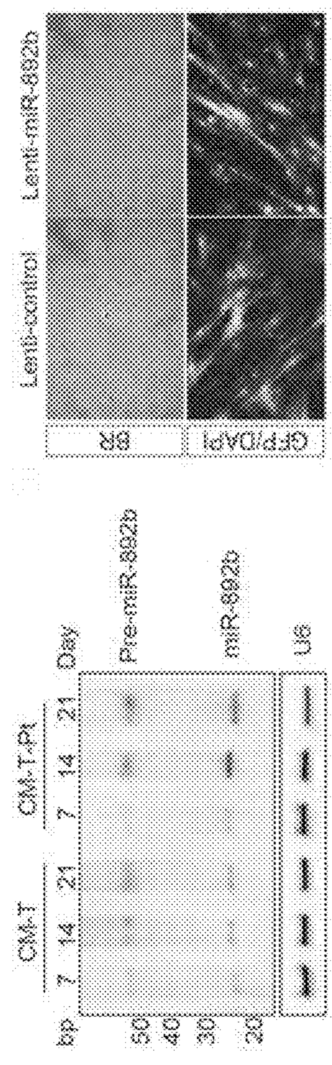
FIG.3B
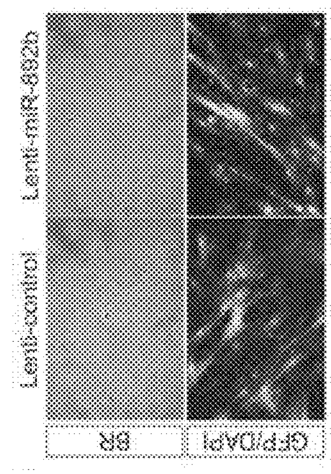
FIG.3C
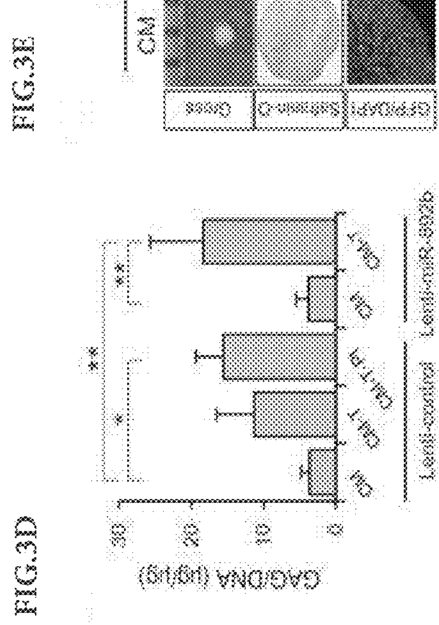
FIG.3D
FIG.3E
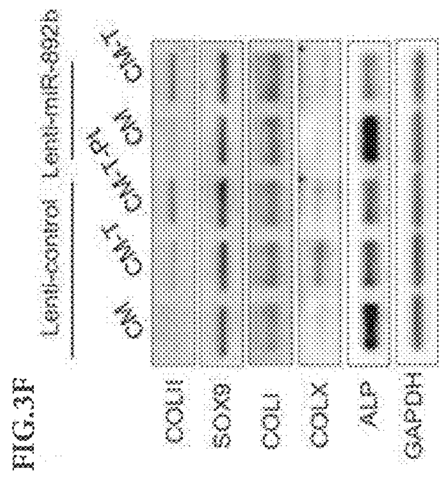
FIG.3F FIG.4A
FIG.4B
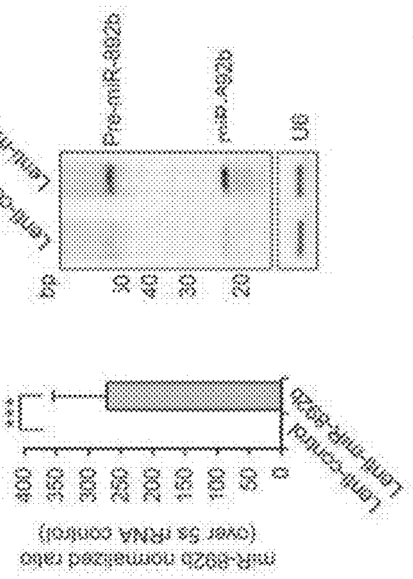
FIG.4C
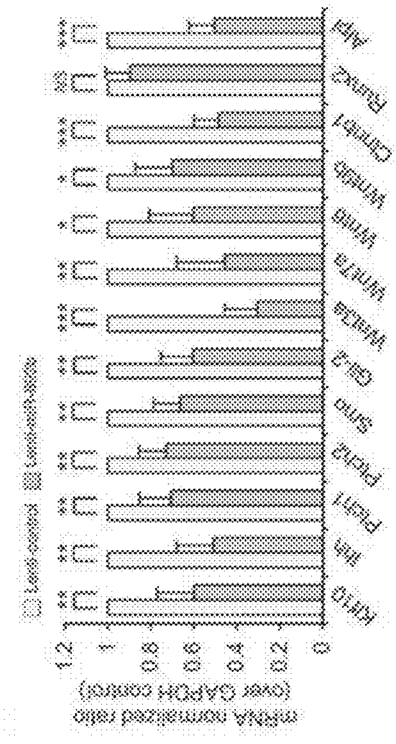
FIG.4D
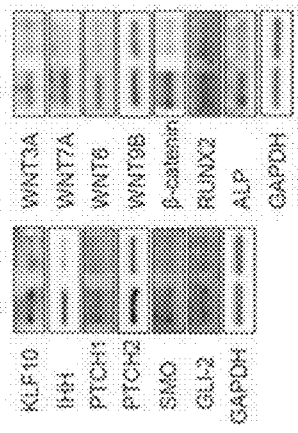
FIG.4E
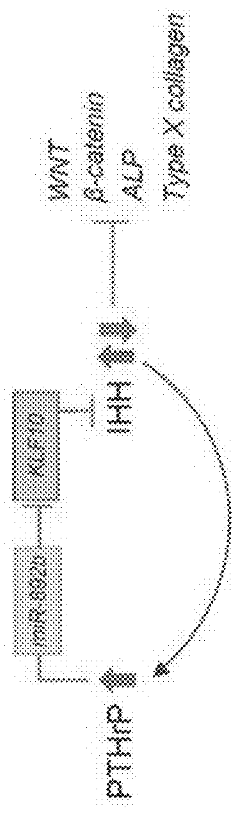

FIG.7A
pLKO.1-shKLF10
FIG.7B
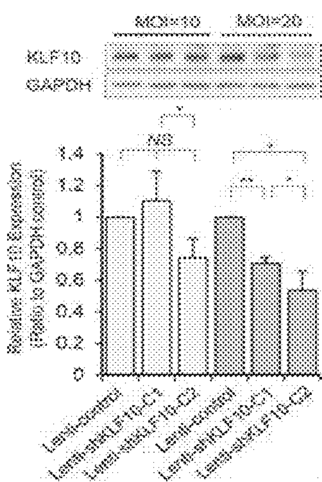
FIG.7C
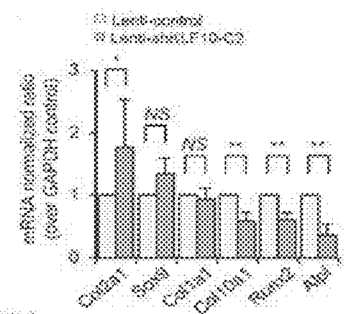
FIG.7D
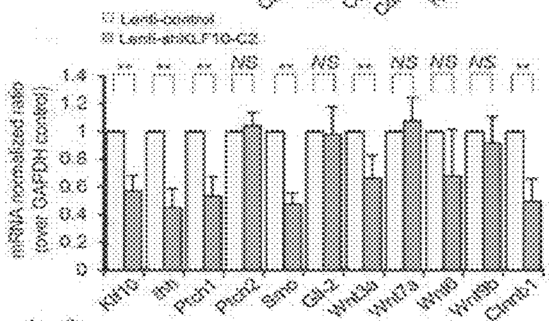
FIG.7E
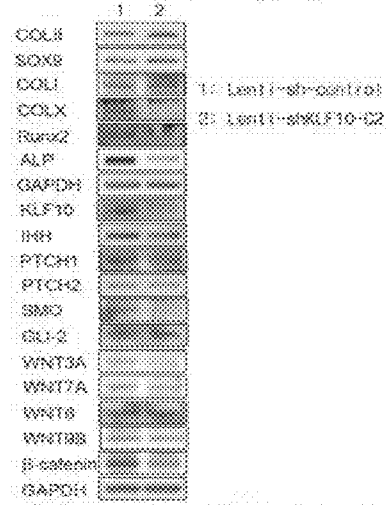
FIG.7F
shKLF10-C1
5'-CCGGGAGTATGTATTCCTGGAACAACTCGAGTTGTTCCAGGAATACATACTCTTTTTG-3' (SEQ ID NO: 2)
3'-CTCATACATAAGGACCTTGTTGAGCTCAACAAGGTCCTTATGTATGAGAAAAACTTAA-5' (SEQ ID NO: 45)
shKLF10-C2
5'-CCGGGAACCCTCTCAAGTGTCAAATCTCGAGATTTGACACTTGAGAGGGTTCTTTTTG-3' (SEQ ID NO: 3)
3'-CTTGGGAGAGTTCACAGTTTAGAGCTCTAAACTGTGAACTCTCCCAAGAAAAACTTAA-5' (SEQ ID NO: 46)

FIG. 8A
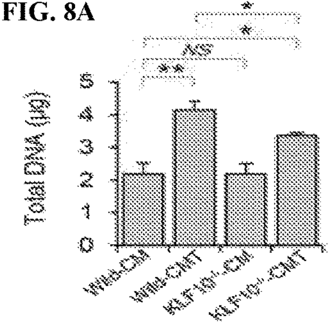
FIG. 8B
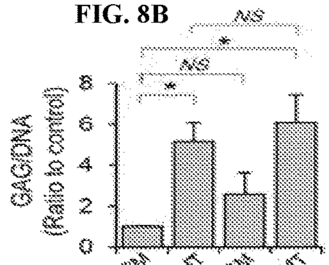
FIG. 8C
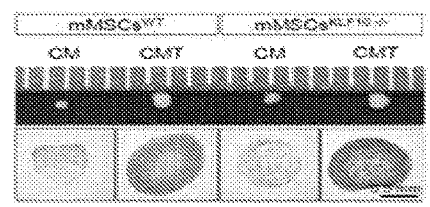
FIG. 8D
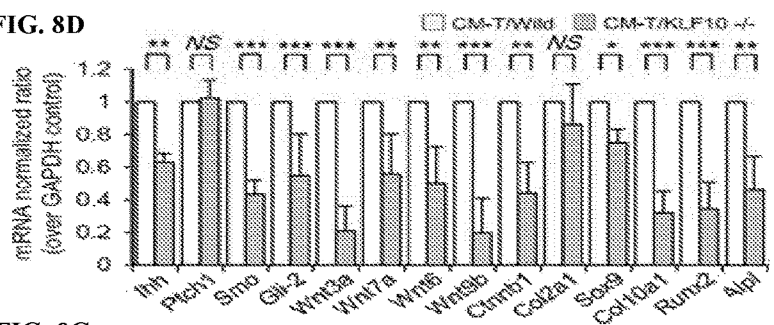
FIG. 8F
FIG. 8G
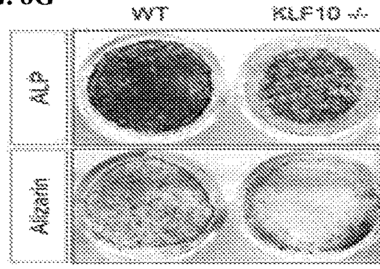
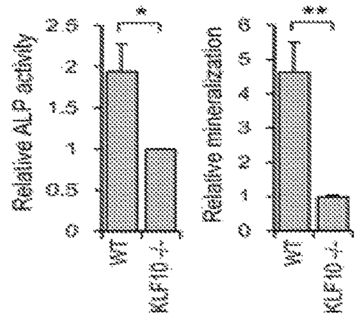
FIG. 8E
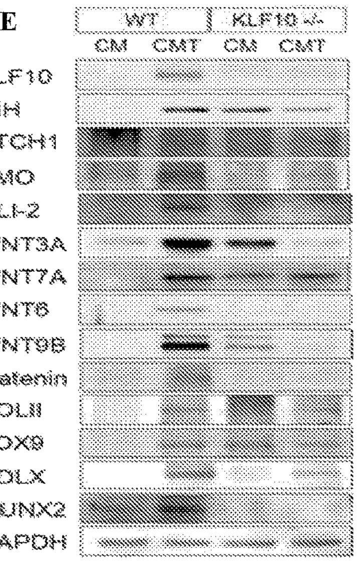

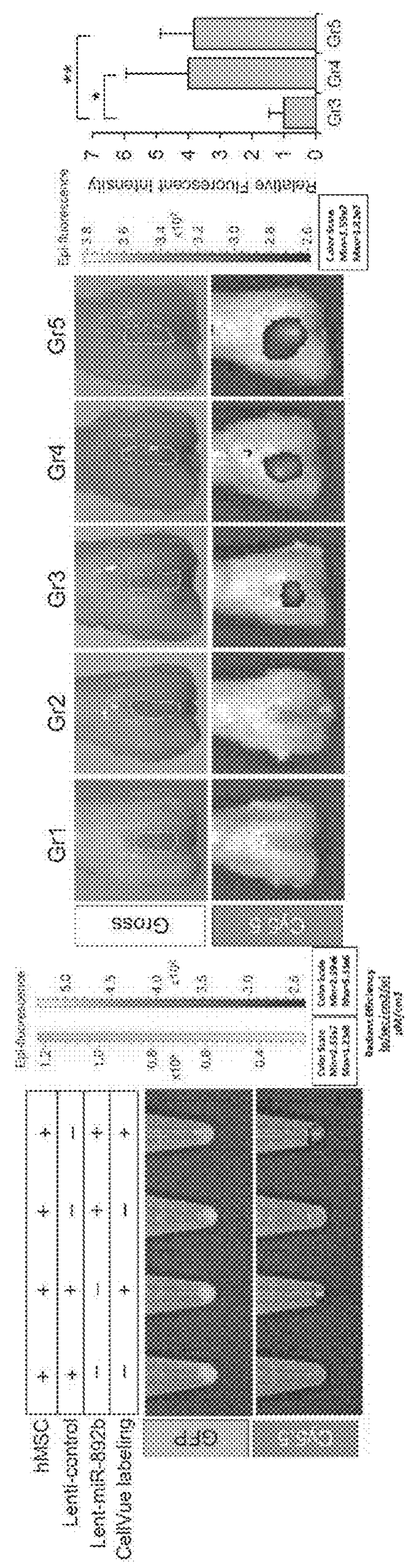
FIG.9A
FIG.9B
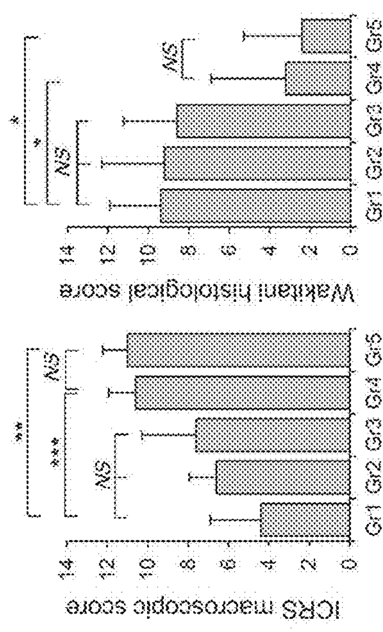
FIG.9C
FIG.9D
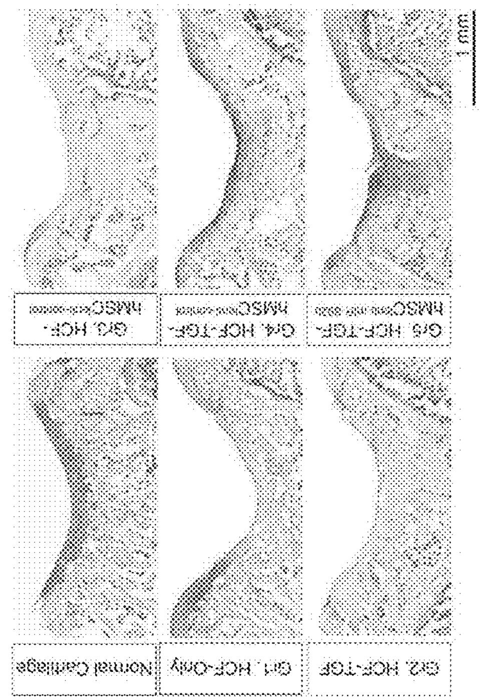
FIG.9E

COMPOSITION FOR PROMOTING CHONDROCYTE DIFFERENTIATION OR TREATING CARTILAGE DISEASES, CONTAINING KLF10 EXPRESSION INHIBITOR, AND METHOD FOR PROMOTING CARTILAGE DIFFERENTIATION BY USING SAME

STATEMENT REGARDING GOVERNMENT RIGHTS

The present invention was undertaken with the support of 1) Transformed stem cells by gene delivery of a specific microRNA-nonviral vector for inhibiting chondrocyte hypertrophy No. 2014R1A1 A2054855 grant funded by the National Research Foundation of Korea (NRF) and 2) Development of gene vector and animal model for the cell therapy of osteoarthritis No. 1465015665 grant funded by the Korea Health Industry Development Institute (KHIDI).

CROSS-REFERENCE TO RELATED APPLICATIONS

This application is a 371 of PCT/KR2014/013006, filed Dec. 30, 2014, which claims the benefit of Korean Patent Application Nos. 10-2013-0168736, filed Dec. 30, 2013 and 10-2014-0191592, filed Dec. 29, 2014, the contents of each of which are incorporated herein by reference.

FIELD OF THE INVENTION

The present invention relates to a Krueppel-like factor 10 (KLF10) gene expression inhibitor promoting chondrocyte differentiation, and, more particularly, to a composition for treating a cartilage disease or promoting chondrocyte differentiation, wherein the composition comprises a KLF10 gene expression inhibitor for promoting chondrocyte differentiation and inhibiting chondrocyte hypertrophy and dedifferentiation.

BACKGROUND ART

There have been many attempts to ease the difficulty of healing damaged articular cartilage, since, once damaged, the articular cartilage cannot be regenerated into original tissue. Currently, for advanced degenerative arthritis, the standardized treatment is to remove the affected cartilage and bone and replace them with an artificial joint consisting of a metal(s) and a polyethylene, but the durability of such an artificial joint becomes an issue when it is implanted into a relatively young patient in his/her 60s or younger. The development of damaged cartilage is caused by osteoarthritis which brings a traumatic loss or gradual destruction of articular cartilage tissue, and, despite the high incidence thereof, the regeneration of damaged cartilage into original tissue thereof, i.e., hyaline cartilage, is difficult, and not much is known about the molecular mechanism of cartilage regeneration.

Conventional methods of treating a damaged joint include medication, autologous chondrocyte implantation, bone marrow drilling, artificial joint replacement, and the like. Among them, conservative treatment such as medication is limited to the restoration of a limited number of functions by alleviating symptoms, and autologous chondrocyte implantation used for treating a traumatic loss of articular cartilage causes damage in the donor site by harvesting a bone-cartilage piece therefrom and the amount collectable is limited. In addition, bone marrow drilling performed for osteoarthritis with moderate progression results in the regeneration of fibrous cartilage instead of the original cartilage tissue, i.e., hyaline cartilage, thus generating poor clinical results. Moreover, the durability of an artificial joint can also be an issue when the artificial joint is implanted into a young patient, although artificial joint replacement is currently the standardized treatment for advanced osteoarthritis.

To solve aforementioned problems, stem cells offering the benefit of self-replication, differentiation into various tissues, and easy harvesting of a large amount without causing the functional disability of the donor site were recently recognized as ideal sources of cells for cell therapy and are actively researched. However, still, there is a lack of clear knowledge of cartilage formation in terms of the factors, environment, and the like.

Stem cells for articular cartilage regeneration are characterized by a self-proliferation ability and a differentiation ability, i.e., an ability to be differentiated into cells constituting a particular tissue, and have been recently proposed as new sources of cells to be applied in articular cartilage treatment. Therefore, theoretically, such stem cells may be used to ease the limitations that conventional cell therapy using chondrocytes have and to treat the overall degeneration and damage of articular cartilage. In addition, the use of adult mesenchymal stem cells and mesenchymal progenitor cells are free from ethical issues and allograft rejection.

However, since not all adult mesenchymal stem cells completely differentiate into chondrocytes at the same time, ways to induce their differentiation into homogeneous chondrocytes are needed, and, for the differentiation of mesenchymal stem cells into cartilage, ways to inhibit cell hypertrophy, which is a prodromal sign of the apoptosis of cells induced into cartilage and of bone differentiation, by precisely controlling the same is strongly needed to apply chondrocytes differentiated from stem cells for cell therapy.

The hypertrophy of chondrocytes is a process that occurs during ontogenesis or in every stage of chondrocyte destruction and bone formation during endochondral ossification in a growth plate and is always observed during the maturation of chondrocytes other than articular chondrocytes. However, since cartilage tissue engineering aims to regenerate articular cartilage, regenerated cartilage should exhibit the properties of hyaline cartilage found in a normal joint and should not experience hypertrophy.

The parathyroid hormone-related protein (PTHrP) is a peptide that is involved in chondrocyte proliferation and maturation in a growth plate, and is secreted within cartilage surrounding a joint and diffuses to act on a prehypertrophic chondrocyte in a growth plate, thereby inhibiting the formation of the Indian hedgehog (IHH) protein that promotes chondrocyte maturation, thus maintaining the phenotype of a chondrocyte and inhibiting chondrocyte hypertrophy.

However, until now, any reaction mechanism of IHH protein generation inhibition by PTHrP has not been explained in terms of a precise molecular biological mechanism.

SUMMARY OF THE INVENTION

Technical Problem

The present inventors were the first to reveal that the cartilage differentiation ability of bone marrow stem cells can be greatly improved by regulating Indian hedgehog (IHH) protein expression or activity by controlling Krueppel-like factor 10 (KLF10) expression or activity, and thereby completed the present invention.

In addition, the present inventors revealed that the parathyroid hormone-related protein (PTHrP) induces the expression of miR-892b, which is microRNA (miRNA), and explained that such miR-892b can sequentially control IHH protein expression by inhibiting the expression of KLF10 gene, which is an upstream regulatory protein of the IHH protein.

However, the technical objectives of the present invention are not limited to those mentioned above, and other objectives not addressed herein will be clearly understood by those skilled in the art from the following descriptions.

Technical Solution

In order to accomplish the aforementioned objectives of the present invention, the present invention provides a composition for promoting chondrocyte differentiation, wherein the composition comprises a Krueppel-like factor 10 (KLF10) gene expression inhibitor.

In addition, the present invention provides a composition for treating a cartilage disease, wherein the composition comprises a KLF10 gene expression inhibitor.

In one embodiment of the present invention, the KLF10 gene may consist of a base sequence encoding an amino acid sequence represented by SEQ ID NO. 1.

In another embodiment of the present invention, the expression inhibitor may be selected from the group consisting of microRNA (miRNA), small interfering RNA (siRNA), and short hairpin RNA (shRNA), which complementarily bind to mRNA of the KLF10 gene.

In still another embodiment of the present invention, the miRNA may be a miR-892b gene consisting of a base sequence of SEQ ID NO. 4.

In yet another embodiment of the present invention, the shRNA may consist of a base sequence of SEQ ID NO. 2 or 3.

In an additional embodiment of the present invention, the RNA may be one that has been inserted into an expression vector.

In another additional embodiment of the present invention, the composition may inhibit chondrocyte hypertrophy and dedifferentiation.

In still another additional embodiment of the present invention, the cartilage disease may be a disease selected from the group consisting of degenerative arthritis, rheumatoid arthritis, a fracture, damaged muscle tissue, plantar fasciitis, lateral epicondylitis, calcific tendinitis, fracture nonunion, and a damaged joint due to trauma.

In addition, the present invention provides a chondrocyte therapeutic agent comprising the aforementioned composition.

In addition, the present invention provides a method of promoting the differentiation of a bone marrow stem cell into a chondrocyte, wherein the method comprises a process of expressing the aforementioned composition in the bone marrow stem cell.

In addition, the present invention provides a method of screening a differentiation promoter or chondrocyte therapeutic agent, wherein the method comprises the following processes of:

(a) treating a chondrocyte with a candidate substance;

(b) determining a KLF10 expression level after the treatment with a candidate substance; and (c) selecting candidate substances with which the KLF10 expression level is seen to be reduced compared to a control group not treated with a candidate substance.

In one embodiment of the present invention, the expression level of the process (b) may be determined by any one method selected from the group consisting of immunoprecipitation, radioimmunoassay (RIA), enzyme-linked immunosorbent assay (ELISA), immunohistochemical analysis, real-time PCR, qRT-PCR, western blotting, and fluorescence-activated cell sorting (FACS).

Also, the present invention provides a method of treating a cartilage disease, wherein the method comprises a process of administering the aforementioned composition to a subject.

In addition, the present invention provides a method of promoting chondrocyte differentiation, wherein the method comprises a process of administering the aforementioned composition to a subject.

In one embodiment of the present invention, the administration may be oral administration, intravenous injection, intraperitoneal injection, intramuscular injection, intra-arterial injection, subcutaneous injection, or the like.

In another embodiment of the present invention, the subject may be a mammal comprising a human.

Further, the present invention provides a use of the aforementioned composition for promoting chondrocyte differentiation or treating a cartilage disease.

Advantageous Effects

When expressed in a bone marrow stem cell to induce differentiation into a chondrocyte, the Krueppel-like factor 10 (KLF10) expression inhibitor of the present invention exhibits an excellent efficacy of promoting differentiation into a chondrocyte and inhibiting cartilage hypertrophy.

BRIEF DESCRIPTION OF DRAWINGS

FIG. 1A shows miRNA microarray results for measuring a change in miRNA expression with or without an addition of the parathyroid hormone-related protein (PTHrP) when the differentiation of a human bone marrow stem cell into cartilage is induced.

FIG. 1B shows the results of analyzing the expression patterns of the has-miR-892b, has-miR-1305, has-miR-1288, and has-miR-877*.

FIG. 1C shows the chromosomal location and assession No. of SEQ ID Nos: 4, 5, 7 and 8.

FIGS. 3A-3F show the results of analyzing the cartilage differentiation promotion and hypertrophy inhibition efficacies of miR-892b expression when the differentiation of a miR-892b lentivirus-infected human bone marrow stem cell into cartilage is induced.

FIG. 3A shows the results of change in relative miR-892b expression due to a PTHrP treatment in human bone marrow stem cell.

FIG. 3B shows the results of the RNA expression level of Pre-miR-892b and miR-892b in northern blotting.

FIG. 3C shows the results of infecting human bone marrow stem cells with Lenti-miR-892b.

FIG. 3D shows the results of GAG/DNA ratio in groups of human bone marrow stem cells infected with a miR-892 virus.

FIG. 3E shows the results of comparing the appearance of pellets.

FIG. 3F shows the results of the protein expression level of COL II, SOX9, COL I, COLX, ALP and GAPDH.

FIGS. 4A-4E show the results of analyzing a mechanism of cartilage differentiation efficiency enhancement and hypertrophy inhibition when miR-892b is overexpressed.

FIG. 4A shows the results of miR-892b RNA expression ratio in groups of human bone marrow stem cells infected with a miR-892b virus using RQ-PCR.

FIG. 4B shows the results of miR-892b RNA expression ratio in groups of human bone marrow stem cells infected with a miR-892b virus using northern blot.

FIG. 4C shows the results of mRNA expression ratio of Klf10, Ihh, Ptch1, Ptch2, Smo, Gli-2, Wnt3a, Wnt7a, Wnt6, Wnt9b, Ctnnb1, Runx2 and Alp1 in groups of human bone marrow stem cells infected with a miR-892b virus.

FIG. 4D shows the results of protein expression level KLF10, IHH, PTCH1, PTCH2, SMO, GLI-2, WNT3A, WNT7A, WNT6, WNT9B, CTNNB1, RUNX2 and ALPL in groups of human bone marrow stem cells infected with a miR-892b virus.

FIG. 4E shows a schematic diagram of new PTHrP-IHH negative feedback inhibition.

FIG. 5A shows the binding sites of a KLF10 (SEQ ID NO: 41) or WNT6 gene (SEQ ID NO: 42) for miR-892b (SEQ ID NO: 4) within a 3'UTR.

FIG. 5B shows the critical miR-892b binding sites of KLF10 WT (SEQ ID NO: 41), KLF10-MUT (SEQ ID NO: 43), WNT6 WT (SEQ ID NO: 42) or WNT6 MUT (SEQ ID NO: 44) within a 3'UTR.

FIG. 5C shows the luciferase activity KLF10-3'UTR and WNT6-3' UTR.

FIG. 6A shows a schematic diagram of the preparation of pECFP-C1-hKLF10. FIG. 6B shows the distribution of expressed KFL10 within the human bone marrow stem cells transfected with hMSC-pECFP-hKLF10.

FIG. 6C shows the results of mRNA expression of Klf10, Ihh, Ptch1, Runx2 and Alp1.

FIG. 6D shows the protein expression ratio of IHH.

FIGS. 7A-7F show the results of analyzing cartilage differentiation induction efficacy when KLF10 is knocked down using short hairpin RNA (shRNA).

FIG. 7A shows a schematic diagram of pLKO.1-shKLF10.

FIG. 7B shows the results of protein expression level of KFL10.

FIG. 7C shows the results of mRNA expression level of Col2a1, Sox9, Col1a1, Col10a1, Runx2 and Alp1.

FIG. 7D shows the results of mRNA expression level of Klf10, Ihh, Ptch1, Ptch2, Smo, Gli-2, Wnt3a, Wnt7a, Wnt6, Wnt9b and Ctnnb1.

FIG. 7E shows the results of protein expression level of COL2A1, SOX9, COL1A1, COL10A1, RUNX2, ALPL, KLF10, IHH, PTCH1, PTCH2, SMO, GLI-2, WNT3A, WNT7A, WNT6, WNT9B and CTNNB1.

FIG. 7F shows a schematic diagram of KLF10 shRNA base sequences.

FIGS. 8A-8G show the results of analyzing cartilage differentiation induction efficacy in a KLF10 knockout mouse.

FIGS. 8A and 8B shows the result of total DNA and GAG/DNA level in KLF10 wildtype and K/O mouse cartilage pellets.

FIG. 8C shows the rate of Safranin-O staining of groups KLF10 wildtype and K/O bone marrow stem cells.

FIG. 8D shows results of the mRNA expression levels of signaling proteins in the IHH signaling pathway and canonical Wnt signaling pathway.

FIG. 8E shows the results of the protein expression levels of signaling proteins in the IHH and canonical Wnt signaling pathway.

FIG. 8F shows the KLF10 and IHH expression in KLF10 wildtype or K/O bone marrow stem cells.

FIG. 8G shows the results of ALP activity and mineralization in KLF10 wildtype or K/O bone marrow stem cells.

FIGS. 9A-9E show the results of transplanting a miR892b-expressing bone marrow stem cell into a rat cartilage defect model to examine the cartilage regeneration efficacy.

FIG. 9A shows the distribution of transplanted cells within a living body.

FIG. 9B shows the relative fluorescent intensity between groups.

FIG. 9C shows the analyzed results of ICRS macroscopic score.

FIG. 9D shows the analyzed results of Wakitani histological score.

FIG. 9E shows the rate of Safranin-O staining of groups.

DETAILED DESCRIPTION OF THE INVENTION

Figure 2:
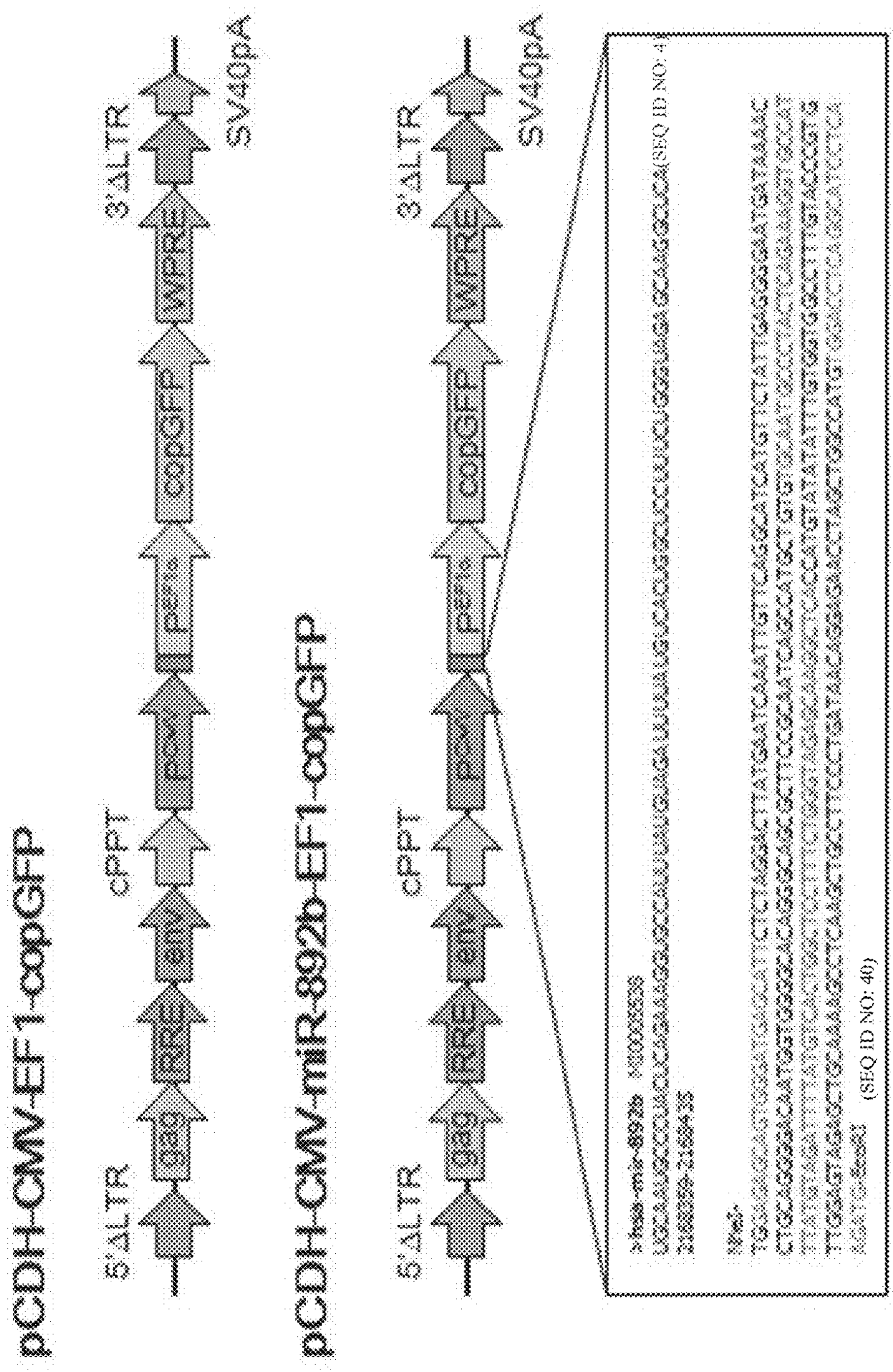
FIG. 2 is a schematic diagram showing the preparation of a recombinant lentivirus for expressing miR-892b in a human bone marrow stem cell.

The present invention provides a composition comprising a Krueppel-like factor 10 (KLF10) gene expression inhibitor for promoting chondrocyte differentiation and a composition comprising a KLF10 gene expression inhibitor for treating a cartilage disease.

The present inventors were the first to reveal that the KLF10 gene expression inhibitor exhibits an activity inhibiting chondrocyte hypertrophy and dedifferentiation by reducing the expression of Indian hedgehog (IHH), which is a substance initiating hedgehog signaling of the IHH signaling pathway.

The KLF10 gene is a human (*Homo sapiens*) KLF10 gene. The KLF10 gene preferably consists of a base sequence encoding an amino acid sequence represented by SEQ ID NO. 1 and more preferably consists of a base sequence represented by SEQ ID NO. 39, but is not limited thereto.

The expression inhibitor may be any substance that can inhibit KLF10 expression or activity. The expression inhibitor may be microRNA (miRNA), small interfering RNA (siRNA), short hairpin RNA (shRNA), or the like which complementarily binds to an mRNA of a KLF10 gene, wherein the miRNA is preferably a miR-892b gene consisting of a base sequence of SEQ ID NO. 4 and the shRNA preferably consists of a base sequence of SEQ ID NO. 2 or 3, but they are not limited to those mentioned above.

In addition, the present invention also comprises a mutant of the aforementioned base sequence, and, more particularly, it may comprise a base sequence that is identical to the aforementioned base sequence with 70% sequence identity or more, more preferably by 80% sequence identity or more, even more preferably by 90% sequence identity or more, and most preferably by 95% sequence identity or more. The "% sequence identity" for a polynucleotide is determined by comparing a comparison region with two optimally aligned sequences, and a part of the polynucleotide sequence in the comparison region may comprise an addition or deletion (i.e. a gap) compared to a reference sequence (not comprising an addition or deletion) for the optimal alignment of the two sequences.

In the present invention, RNA as the expression inhibitor may be one that has been inserted into a recombinant expression vector. The term a "recombinant expression vector" refers to a bacterial plasmid, a phage, a yeast plasmid, a plant cell virus, a mammalian cell virus, or another vector, and, in general, may be any vector as long as it can be replicated and stabilized within a host. An important feature of such an expression vector is that it has an origin of replication, a promoter, a marker gene, and a translation control element. That is, the expression vector may be a gene construct that is capable of expressing a desired protein in a suitable host cell and comprises essential regulatory elements operably linked so that the inserted gene is expressed.

In addition, the term "recombinant" refers to a cell replicating a heterologous nucleic acid, expressing the nucleic acid, or expressing a peptide, a heterologous peptide, or a protein encoded by a heterologous peptide. A recombinant cell can express, in either a sense or antisense form, a gene or gene segment that would not be found otherwise in a natural form of the aforementioned cell. Such a recombinant cell can also express a gene found in a natural form of the cell, but, in this case, the gene has been modified and reintroduced into the cell by artificial means.

An expression vector comprising the aforementioned RNA sequence and a suitable transcription/translation controlling signal may be constructed by a method known to those skilled in the art. Such a method comprises in-vitro recombinant DNA techniques, DNA synthesis techniques, in-vivo recombinant techniques, and the like. The DNA sequence can be effectively connected to a suitable promoter within an expression vector. Also, an expression vector may comprise a ribosome binding site and a transcription terminator as a translation initiation site.

Examples of the expression vector of the present invention may comprise a plasmid vector, a cosmid vector, an episomal vector, a virus vector, and the like. Preferably, the expression vector is a virus vector. The virus vector may be a vector derived from a retrovirus, a lentivirus, an adenovirus, an adeno-associated virus, a herpes simplex virus, a Sendai virus, and the like, and is preferably a lentivirus vector and more preferably a plasmid vector such as pCDH, pECFP, or pLKO, but is not limited thereto.

In the present invention, a "cartilage disease" refers to a disease caused as cartilage, cartilage tissue, and/or joint tissue (synovia, joint capsules, subchondral bones, etc.) are injured by a mechanical irritation or an inflammatory response, and comprises a disease associated with damaged cartilage. Such a cartilage disease may be, but is not limited to, degenerative arthritis, rheumatoid arthritis, a fracture, damaged muscle tissue, plantar fasciitis, lateral epicondylitis, calcific tendinitis, fracture nonunion, and a damaged joint due to trauma.

In addition, the present invention may provide a cell therapeutic agent comprising the aforementioned composition. A cell therapeutic agent is a cell and a tissue prepared through isolation from a human body, culturing, and a special treatment, and is a medicine used for therapeutic, diagnostic, and preventive purposes. It refers to a medicine used for therapeutic, diagnostic, and preventive purposes aimed at restoring the functions of a cell or tissue through a series of actions such as multiplying and screening a autologous, homologous, or heterologous living cell in vitro and modifying the biological characteristics of the cell in other ways.

The cell therapeutic agent may be directly injected into a joint of a patient or implanted together with a scaffold after three-dimensional (3D) culturing according to a well-known method, and the number of cells to be administered may be controlled, considering various associated factors such as the disease to be treated, the severity of the disease, the route of administration, and the body weight, age, and gender of the patient.

In addition, the composition or cell therapeutic agent of the present invention may be applied to a damaged portion of cartilage by being inoculated on a support for cartilage formulation. Such a support should be biocompatible, bioabsorbable, or capable of remodeling, and offer a framework for facilitating the growth of new tissue. In addition, the support should exhibit material and mechanical properties compatible with articular cartilage functions. A support providing an environment for 3D culturing affects the ultimate quality of the cartilage tissue prepared in a tissue-engineered manner as well as the proliferation and differentiation of the inoculated cells. Currently, various materials synthesized or derived from a natural material are used as a suitable support. Such supports take various forms such as a sponge, a gel, a fiber, and a microbead, and the most common form among them is a porous structure capable of improving the rate of cell adhesion and maintaining a large surface-tension-to-volume ratio.

The composition or cell therapeutic agent of the present invention may be applied to a damaged portion of cartilage of a human or non-human organism, e.g., a non-human mammal such as a cow, monkey, bird, cat, mouse, rat, hamster, pig, dog, rabbit, sheep, and horse, to promote cartilage regeneration (differentiation), or be administered into a joint by injection for treating a cartilage disease.

Therefore, the present invention may provide a method of promoting the differentiation of a bone marrow stem cell into cartilage or treating a cartilage disease, wherein the method comprises a process of expressing the composition in the bone marrow stem cell.

Further, the present invention may provide a method of screening a chondrocyte differentiation promoter or chondrocyte therapeutic agent, wherein the method comprises the following processes.

Specifically, the screening method preferably comprises, but is not limited to, the processes of:

(a) treating a chondrocyte with a candidate substance;

(b) determining a KLF10 expression level after the treatment with a candidate substance; and (c) selecting candidate substances with which the KLF10 expression level is seen to be reduced compared to a control group not treated with a candidate substance.

In the method, the expression level of process (b) is preferably determined by a method such as immunoprecipitation, radioimmunoassay (RIA), enzyme-linked immunosorbent assay (ELISA), immunohistochemical analysis, real-time PCR, qRT-PCR, western blotting, or fluorescence-activated cell sorting (FACS), but the method is not limited to those listed above, and any well-known method in the art of determining the amount of transcriptomes and proteins coded from such transcriptomes may be used.

EXAMPLES

Hereinafter, exemplary examples of the invention will be described for promoting an understanding of the invention.

However, the following examples should be considered in a descriptive sense only and the scope of the invention is not limited to the following examples.

Example 1

Analysis of Change in miRNA Expression with or without Addition of PTHrP when Differentiation of Human Bone Marrow Stem Cell into Cartilage is Induced A miRNA microarray analysis was carried out to observe a change in a miRNA expression level as a result of a treatment with PTHrP when inducing the differentiation of human bone marrow stem cell into cartilage. First, while carrying out a treatment with TGF-β3 for total of 4 weeks to induce the differentiation of human bone marrow stem cells into cartilage, the cells were divided into a group additionally treated with PTHrP for the last 1 or 2 weeks and a group not treated with PTHrP, and RNA was separated from a cell pellet in which cartilage differentiation had been induced, and then, cDNA labeled with a Cy3-fluorescent dye was synthesized, from the RNA, for the entire miRNA. Then, the cDNA was hybridized on an Agilent human miRNA microarray chip coated with about 15,000 different DNA base sequences complementary to human miRNA to separate, through Cy3 fluorescence image analysis, miRNA whose expression is amplified by 1.5 times or more only by a treatment with PTHrP.

TABLE 1

| Name | Sequence | Position on chromosome | Accession No. | SEQ ID NO. |
|---|---|---|---|---|
| hsa-miR-892b | CACUGGCU CCUUUCUG GGUAGA | chrX: 145078716-145078792 | MI0005538 | 4 |
| hsa-miR-1288-5P | GCAGAUCA GGACUGUA ACUCACC | chr17: 16185378-16185392 | MI00..06432 | 5 |
| hsa-miR-1288-3P | UGGACUGC CCUGAUCU GGAGA | chr17: 16185378-16185392 | MI0006432 | 6 |
| hsa-miR-1305 | UUUUCAAC UCUAAUGG GAGAGA | chr4: 183090500-183090517 | MI0006372 | 7 |
| hsa-miR-877* | UCCUCUUC UCCCUCCU CCCAG | chr6: 030552182-030552194 | MI0005561 | 8 |

When the rate of a change in a miRNA expression level is determined to identify the miRNA whose expression level decreases (green) and the miRNA whose expression level increases (red), as appears in FIG. 1A, 4 types of miRNA (hsa-miR-892b, hsa-miR-1305, hsa-miR-1288, hsa-miR-877*) exhibited an 1.5-fold or more increase in their expression only by a treatment with PTHrP when cartilage differentiation was induced, and the RNA base sequences of the 4 types of miRNA with increased expression are as shown in the above Table 1. In addition, as shown in FIG. 1B, the results of analyzing the expression patterns of the 4 types of miRNA over time show that, unlike other miRNA exhibiting a gradually increasing pattern, miR-892b temporarily increased only for 1 week after the treatment.

With this, it was found that miR-892b expression temporarily increased only for 1 week due to a PTHrP treatment and did not increase thereafter even with a PTHrP treatment.

Example 2

Analysis of Cartilage Differentiation and Hypertrophy Inhibition Efficacies of Using Recombinant Lentivirus Expressing miR-892b In order to prepare a recombinant lentivirus expressing miR-892b, first, a 340-bp DNA segment (SEQ ID NO. 40, that comprises pre-mature miR-892b acquired from human bone marrow stem cell DNA through genomic PCR) and a pCDH lentivirus vector were cut by being treated respectively with NheI and EcoRI restriction enzymes and were connected to each other to prepare a pCDH-CMV-miR-892b-EF1-copGFP recombinant vector as shown in FIG. 2. Then, the recombinant vector and a lentiviral packaging system comprising 3 types of packaging vectors (pLP1, pLP2, pVSVG) in a 1:1.5:1 ratio for lentivirus production were simultaneously transfected, in a 1:3 ratio, into 293FT cells. About 48 hours later, the culture medium was recovered to measure the concentration (titer) of the produced virus and was used for an experiment during which human bone marrow stem cells were subjected to infection.

<2-1> Analysis of Cartilage Differentiation Promotion and Hypertrophy Inhibition Efficacies of miR-892b Expression As shown in FIG. 3A, the results of evaluating, on a weekly basis, a change in miR-892b expression due to a PTHrP treatment for 3 weeks while inducing the differentiation of human bone marrow stem cells into cartilage showed that the miR-892b expression increased 2-fold or more in a group treated with PTHrP (CM-T-P) on about the second week (D14) as compared to a group (CM-T) not treated with PTHrP. Also, as shown in FIG. 3B, the results of northern blotting using RNA samples separated at different times directly showed that the expression level of active miR-892b increased more in a group (CM-T-Pt) treated both with TGF-β3 and PTHrP than in a control group (CM-T) treated only with TGF-β3.

In addition, as seen in FIG. 3C, the results of infecting human bone marrow stem cells with a recombinant lentivirus (miR-892b virus) that was prepared as described above showed that the infection efficiency thereof was similar to that of the control group.

Next, to induce cartilage hypertrophy, cartilage differentiation was induced for 4 weeks in human bone marrow stem cells infected with a miR-892b virus. As appears in FIG. 3D, the results showed a large increase in the GAG/DNA ratio in a group (Lenti-miR-892b:CM-T) infected with a miR-892b virus and treated with TGF-β3, similar to a control group (Lenti-control: CM-T-Pt) infected with a lentivirus and treated with both PTHrP and TGF-β3. Also, as appears in FIG. 3E, the results of comparing the appearance of pellets with the naked eye after inducing cartilage differentiation in each group show that the pellets from all groups are not much different in a morphological sense (FIG. 3E, Gross). However, the results of preparing paraffin blocks out of such pellet tissues, cutting the blocks into 4 μm-thick pieces, and staining the same with 0.1% safranin-O showed that a group (Lenti-miR-892b: CM-T) infected with a miR-892b virus and treated with TGF-β3 had the most prominent cartilage differentiation compared to a control group, exhibiting the highest staining rate (FIG. 3E, safranin-O).

In addition, as shown in FIG. 3F, the results of carrying out 10% SDS-PAGE with a protein obtained from cartilage pellet tissue by extraction using an RIPA buffer, blotting the same on a PVDF membrane, and then carrying out western blotting on the membrane through a reaction with a primary antibody of each of type II collagen (Merck Millipore:

1/500), SOX9 (Abcam: 1/1000), ALP (Abcam: 1/1000), type X collagen (Abcam: 1/1000), and GAPDH (Santa Cruz: 1/1000) and again through a reaction with a secondary antibody of each thereof showed that the expression level of type II collagen (COL II), which is a cartilage differentiation marker, increased and the expression levels of type X collagen (COLX) and alkaline phosphatase (ALP), which are cartilage hypertrophy markers, decreased in a group (Lenti-miR-892b: CM-T) infected with a miR-892b virus and treated with TGF-β3, thus indicating that high cartilage differentiation efficiency is caused by the change in an expression level.

<2-2> Analysis of Mechanism of Cartilage Differentiation Efficiency Promotion and Hypertrophy Inhibition when miR-892b is Overexpressed In order to identify the influence of treating bone marrow stem cells expressing miR-892b with only TGF-β3 and not with PTHrP when the differentiation of a mesenchymal stem cell infected with the recombinant lentivirus of the present invention (miR-892b virus) into cartilage is induced, the amount of miR-892b remaining after inducing cartilage differentiation was determined. First, cDNA for miRNA was synthesized from the RNA separated from each cartilage pellet tissue, and the same was amplified for 5 seconds at 95° C. and for 30 seconds at 60° C. repeatedly for 50 times using a forward primer (SEQ ID NO. 9) for miR-892b shown in Table 2 below and a qPCR universal reverse primer which is available in GenoExplorer™ to carry out RQ-PCR. In this case, for the conversion of the synthesized quantity of miR-892b for each group, RQ-PCR of 5S rRNA (an internal control) was also simultaneously carried out using a forward primer (SEQ ID NO. 10) for 5S rRNA shown in Table 2 below and a qPCR universal reverse primer.

TABLE 2

| Name | Sequence (5' to 3') | SEQ ID NO. |
|---|---|---|
| miR-892b_F | CACTGGCTCCTTTCTGGGTAGA | 9 |
| 5S rRNA_F | GATGGGGCGCGTTCAGGGTGGTAT | 10 |
| Klf10_F | AAAGTTCCCATCTGAAGGCC | 11 |
| Klf10_R | TCACAACCTTTCCAGCTACAG | 12 |
| Ihh_F | ATGAAGGCAAGATCGCTCG | 13 |
| Ihh_R | GATAGCCAGCGAGTTCAGG | 14 |
| Ptch1_F | TCTTGGTGTTGGTGTGGATG | 15 |
| Ptch1_R | ATTGCTGATGGACGTGAGG | 16 |
| Ptch2_F | TGCTCTTTCTGGGACTGTTG | 17 |
| Ptch2_R | AGCTTCTCCTTGGTGTAATGC | 18 |
| Smo_F | GAAGATCAACCTGTTTGCCATG | 19 |
| Smo_R | TTTGGCTCATCGTCACTCTG | 20 |
| Gli-2_F | GTCAGCCTTTGGACACACAC | 21 |
| Gli-2_R | TCTGCTTGTTCTGGTTGGTG | 22 |
| Wnt3a_F | ATCAAGATTGGCATCCAGGAG | 23 |
| Wnt3a_R | CAATGGCGTGGACAAAGG | 24 |
| Wnt7a_F | GGGACTATGAACCGGAAAGC | 25 |
| Wnt7a_R | GGCCTGGGATCTTGTTACAG | 26 |

TABLE 2-continued

| Name | Sequence (5' to 3') | SEQ ID NO. |
|---|---|---|
| Wnt6_F | GAGAGTGCCAGTTCCAGTTC | 27 |
| Wnt6_R | TGATGGCGAACACGAAGG | 28 |
| Wnt9b_F | AGTGCCAGTTTCAGTTCCG | 29 |
| Wnt9b_R | GGAAAGCTGTCTCTTTGAAGC | 30 |
| Ctnnb1_F | GTTCAGTTGCTTGTTCGTGC | 31 |
| Ctnnb1_R | GTTGTGAACATCCCGAGCTAG | 32 |
| Runx2_F | TTACTTACACCCCGCCAGTC | 33 |
| Runx2_R | TATGGAGTGCTGCTGGTCTG | 34 |
| AlpI_F | GACAAGAAGCCCTTCACTGC | 35 |
| AlpI_R | AGACTGCGCCTGGTAGTTGT | 36 |
| GAPDH_F | CACATGGCCTCCAAGGAGTAA | 37 |
| GAPDH_R | GTACATGACAAGGTGCGGCTC | 38 |

As appears in FIGS. 4A and 4B, the results of 4 weeks of inducing the differentiation of bone marrow stem cells infected with a miR-892b lentivirus into cartilage and comparing, using RQ-PCR and a northern blot analysis method in the presence of TGF-β3, the expressed level of miR-892b remaining in a cell as described above showed that the miR-892b expression in bone marrow stem cells infected with a miR-892b lentivirus was as large as about 250 times the miR-892b expression in bone marrow stem cells infected with a negative control lentivirus.

Hence, in order to investigate the effect of miR-892b overexpression within a cell, the expression levels of signaling proteins within the IHH signaling pathway and the subsequent canonical Wnt signaling pathway were amplified for 5 seconds at 95° C. and for 30 seconds at 60° C. using primers (SEQ ID NOs. 11 to 38) listed in the above Table 2, and such amplification was repeated for 60 times to carry out RQ-PCR and western blotting using corresponding antibodies. As appears in FIGS. 4C and 4D, the results showed that miR-892b overexpression resulted in a decrease in KLF10 (a protein predicted as a target of miR-892b) expression and, accordingly, a decrease in IHH (an initiating substance of a hedgehog signal) expression, leading to a decrease in Ptch1, Ptch2, Smo, and Gli-2 expression. Since such results indicate that a hedgehog signal decreases when cartilage differentiation is induced, it can be understood that cartilage hypertrophy is inhibited by miR-892b expression. Also, that Wnt3a, Wnt6, and the like inducing the initiation of the transmission of major canonical Wnt signals decrease after the IHH signaling pathway, resulting in a decrease in the expressed level of β-catenin, which is a final executor of this signaling pathway, proves that cartilage differentiation efficiency increases due to miR-892b overexpression. In addition, it was found that Wnt7a expression observed during a course of chondrocyte dedifferentiation also decreased, indicating that the degree of chondrocyte dedifferentiation may also be reduced by miR-892b overexpression.

The mechanism of PTHrP-IHH negative feedback inhibition that can be understood from the above results is provided in FIG. 4D.

Example 3

Screening and Confirmation of miR-892b Target Genes

Figure 5A:
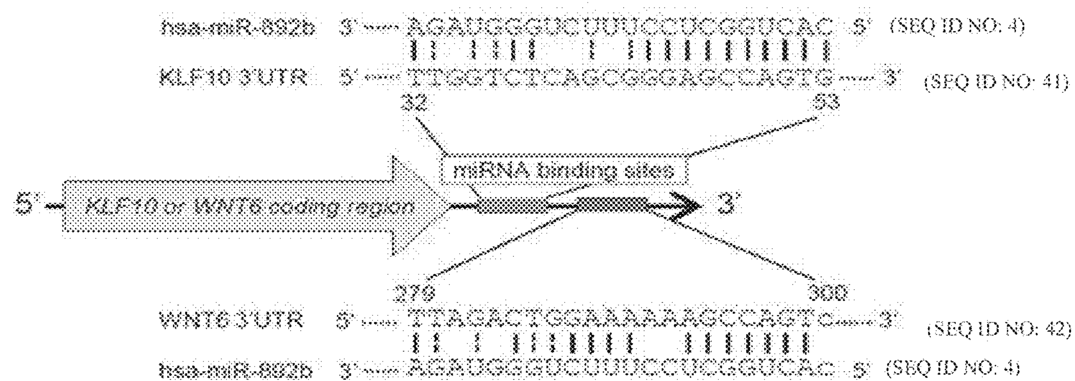
FIGS. 5A-5C show vector cloning for confirming target genes (KLF10 and WNT6) of miR892b and the results of analyzing a degree of target gene (KLF10 and WNT6) expression inhibition by miR892b.
Figure 5B:
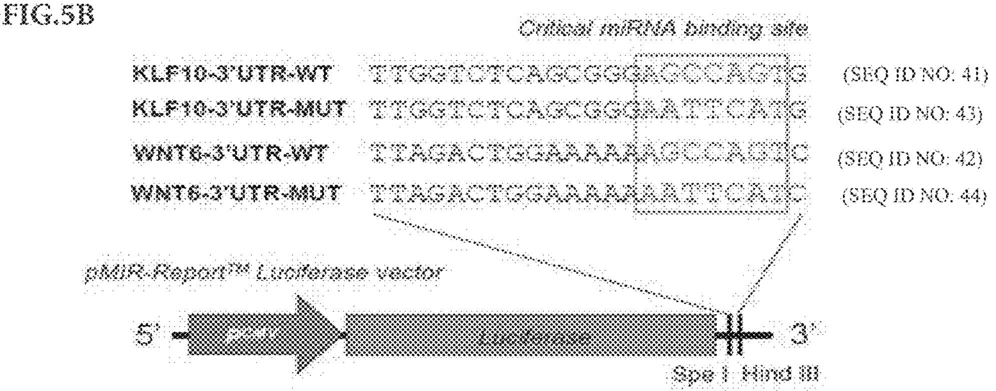
Figure 5C:
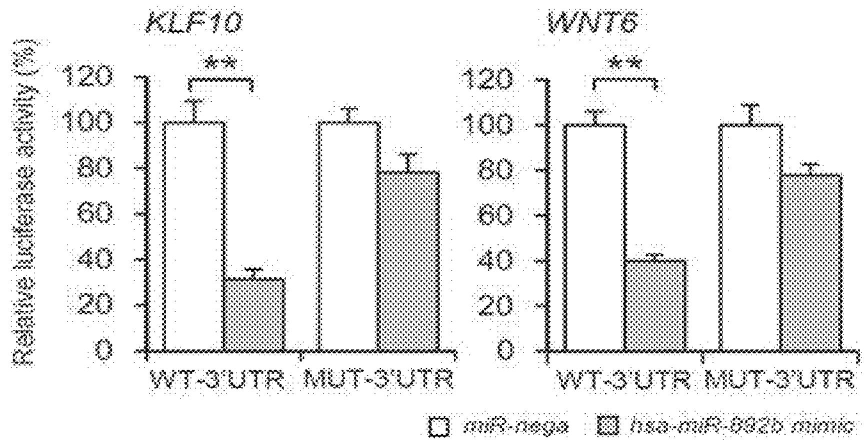

Binding sites of a KLF10 or WNT6 gene for miR-892b within a 3'UTR are as shown in FIG. 5A, wherein the KLF10 or WNT6 gene is predicted as a target gene of miR-892b based on the results of the above Example 2. A gene sequence comprising the binding sites of the KLF10 or WNT6 gene for miR-892b within a 3'UTR and a mutated base sequence within a critical binding site was synthesized to clone a pMIR-luciferase reporter vector (see FIG. 5B; WT, wild type; MUT, mutated). Also, luciferase reporter vectors prepared as described above and a miR-892b mimic or negative miRNA prepared by GE Healthcare Dharmacon Inc. were used to transfect a Hela cell, and, 48 hours later, the degree of target gene expression inhibition by miR-892b was examined. As appears in FIG. 5C, the results showed that, in the case of cells (WT-3'UTR) transfected with the normal KLF10 3'UTR, the rate of luciferase expression in a group transfected with miR-892b (hsa-miR-892b mimic) decreased by about 70% as compared to a group (miR-nega) transfected with negative miRNA, and that such a rate of luciferase expression was again restored in cells (MUT-3'UTR) transfected with the KLF10 3'UTR having a mutated base sequence within a critical site of the KLF10 3'UTR. Similar results were obtained with WNT6, which is another target gene of miR-892b.

Based on these results, it can be understood that KLF10 and WNT6 genes are major target genes whose expression can be controlled by miR-892b.

Example 4

Figure 6C:
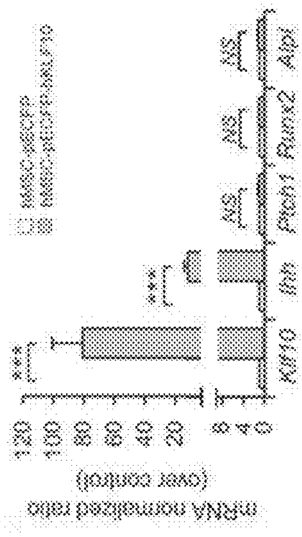
FIGS. 6A-6D show the results of analyzing a change in Indian hedgehog (IHH) expression in a bone marrow stem cell as a result of induced KLF10 overexpression.
Figure 6A:
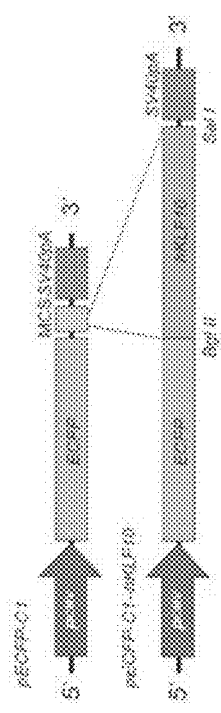

Analysis of Influence of KLF10 Overexpression Induction in Bone Marrow Stem Cells on IHH Expression Human KLF10 cDNA synthesized from the RNA of a human bone marrow stem cell through a reverse transcription reaction was cloned into pECFP (Clontech), which is an overexpression vector in an animal cell, to prepare a KLF10 overexpression vector (pECFP-C1-hKLF10), and a schematic diagram of the process is provided in FIG. 6A. Human bone marrow stem cells were transfected (hMSC-pECFP-hKLF10) using the KLF10 overexpression vector, and, when the distribution of expressed KLF10 within the cells was measured with a fluorescence microscope, as appears in FIG. 6B, the results showed that GFP fused hKLF10 was observed only in the nucleus of cells after expression, which agrees with a nuclear translocation characteristic of a transcription factor after being expressed. In other words, the hKLF10 gene that had been recombined and expressed in an artificial manner was found to be normally functional. Next, bone marrow stem cells (hMSC-pECFP) transfected with a negative control group and bone marrow stem cells (hMSC-pECFP-hKLF10) transfected with a KLF10 overexpression vector were cultured for 6 hours. Then, RNA was separated from the cells to analyze, through RQ-PCR, the gene expression that can be controlled by KLF10. As appears in FIG. 6C, the results showed that IHH expression increased about 12-fold, whereas Ptch1, Runx2, and Alp1 gene expression remained constant without changing, when KLF10 overexpression was induced.

Figure 6D:
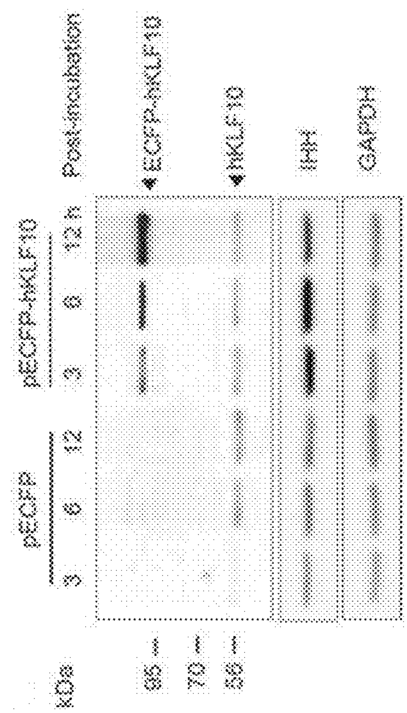
Figure 6B:
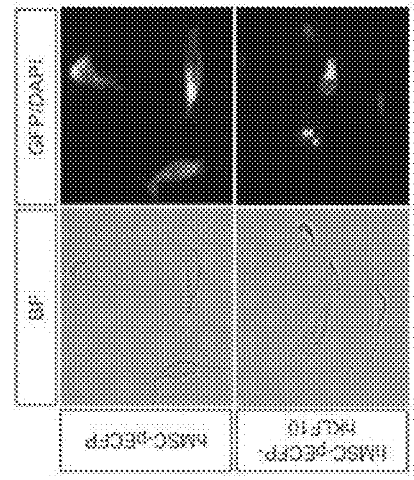

Also, bone marrow stem cells were transfected and proteins were extracted from the cells at a fixed time interval to observe, through western blotting, a change in the IHH expression level due to KLF10 overexpression. As shown in FIG. 6D, the results showed that an increase in the amount of KLF10 protein over time could directly induce an increase in IHH protein expression.

Based on these results, it can be understood that, regardless of a PTHrP treatment, an increase in KLF10 expression could induce an increase in IHH expression.

Example 5

Analysis of Influence of KLF10 Expression Inhibition on Cartilage Differentiation <5-1> Analysis of Cartilage Differentiation Induction Efficacy of Using KLF10 Knockdown Mesenchymal Stem Cells The results obtained from the above examples showed that KLF10 expression inhibition by miR-892b expression increased the efficiency of differentiation of mesenchymal stem cells into cartilage and inhibited hypertrophy. For an additional verification thereof, the results of overexpressing KLF10 shRNA capable of inhibiting KLF10 gene expression by acting directly on the same was analyzed for similarity by comparing with the results of miR-892b overexpression. For this purpose, each of KLF10 shRNA base sequences (shKLF10-C1 and shKLF10-C2) shown in FIG. 7F was inserted into a shRNA expression lentivirus vector (the schematic diagram is provided in FIG. 7A) purchased from Addgene to prepare two different KLF10 shRNA overexpression vectors. Then, bone marrow mesenchymal stem cells were infected with the prepared KLF10 shRNA overexpression lentivirus (Lenti-shKLF10-C1, Lenti-shKLF10-C2) for 12 hours and were cultivated for another 48 hours, and then, the degree of KLF10 expression inhibition within cells was comparatively analyzed for various viral concentrations through western blotting and RQ-PCR. As appears in FIG. 7B, the results showed that the KLF10 expression inhibition efficacy was most excellent when cells were infected with a shKLF10-C2 lentivirus, rather than with shKLF10-C1, at a concentration of MOI=20. Hence, cartilage differentiation was induced for 4 weeks using stem cells infected with a shKLF10-C2 lentivirus in the presence of TGF-β3, and then, the cartilage differentiation efficiency of the stem cells infected with a shKLF10-C2 lentivirus was analyzed by being compared with that of a negative control group. First, the expression levels of cartilage differentiation markers and hypertrophy markers in mesenchymal stem cells whose differentiation was induced were comparatively analyzed through RQ-PCR. As appears in FIG. 7C, the results showed not only that the Col2a1 (a representative cartilage differentiation marker) expression level increased by a valid amount but also that the expression of Col10a1, Runx2, Alp1, etc. (factors related to cartilage hypertrophy) decreased in a group (Lenti-shKLF10-C2) in which shKLF10 had been overexpressed as compared to a negative control group (Lenti-control). In addition, to investigate an influence of shKLF10 overexpression in a differentiated chondrocyte, the expression levels of signaling proteins in the IHH signaling pathway and the subsequent canonical Wnt signaling pathway were analyzed through RQ-PCR and western blotting. As appears in FIGS. 7D and 7E, the results showed that the expression patterns of genes in hedgehog signaling pathways exhibited inhibited gene expression, nearly similar to the case of miR-892b overexpression. However, unlike in the case of miR-892b overexpression, there was no significant decrease in the expression level of Wnt proteins (which induce the initiation of the canonical Wnt signaling pathway) other than Wnt3a.

<5-2> Analysis of Cartilage Differentiation Efficacy of Using KLF10 Knockout Mesenchymal Stem Cells During Induced Cartilage Differentiation In-vitro cartilage differentiation was induced using bone marrow mesenchymal stem cells separated from wild type and KLF10 knockout (K/O) C57BL/6 mice, and then, the cartilage differentiation patterns and degree of hypertrophy inhibition thereof were evaluated. The glycosaminoglycan (GAG) content and DNA content in mouse cartilage pellets, from which cartilage differentiation was induced for 3 weeks, were determined, and, as appears in FIGS. 8A and 8B, the results showed that the GAG/DNA ratio was significantly the highest in a group (KLF$10^{-/-}$-CMT) of KLF10 K/O bone marrow stem cells in which cartilage differentiation was induced in the presence of TGF-β3 as compared to other cell groups. Also, each tissue in which cartilage differentiation was induced was cut, by freezing, into a thickness of 10 μm, and Safranin-O staining was performed thereon. As appears in FIG. 8C, the rate of Safranin-O staining was the highest in a wild-type group (mMSCs$^{wt}$-CMT) or a group (mMSCs$^{KLF10-/-}$-CMT) of KLF10 K/O bone marrow stem cells, from which cartilage differentiation was induced in the presence of TGF-β3, which was a result in agreement with those provided in FIG. 8A.

Next, to examine an influence of a KLF10 knockout in a differentiated chondrocyte, the expression levels of signaling proteins in the IHH signaling pathway and the subsequent canonical Wnt signaling pathway were analyzed through RQ-PCR and western blotting. As appears in FIGS. 8D and 8E, the results showed that a decrease in IHH expression led to a decrease in the expression levels of subsequent signaling proteins and signaling proteins in the canonical Wnt signaling pathway, more prominently than what was shown in the results obtained from miR-892b overexpression.

Hence, in order to identify the correlation between KLF10 and IHH, which is another important point of the present invention but has not been conventionally known, immunofluorescent staining was performed on KLF10 and IHH using a wild-type or KLF10 K/O pellet in which cartilage differentiation had been induced in the presence of TGF-β3. As appears in FIG. 8F, the results showed that the IHH expression level decreased more in a positive control group (a group of KLF10 K/O bone marrow stem cells in which cartilage differentiation had been induced in the presence of TGF-β3) than in a negative control group (a group of wild-type bone marrow stem cells in which cartilage differentiation had been induced in the presence of TGF-β3). Based on the results, a role of KLF10, which was a conventionally unknown transcription factor, as a protein that initiates chondrocyte hypertrophy induction by directly controlling IHH expression during the induced differentiation of adult stem cells into cartilage was revealed for the first time.

In addition, since IHH is known as a protein promoting the differentiation of mesenchymal stem cells into bone, in order to study an influence of mesenchymal stem cells on bone differentiation upon the KLF10 gene knockout, bone differentiation was induced for 14 days in an osteogenic medium (OM) while replacing the differentiation culture medium every 2 to 3 days, and then, alkaline phosphatase (ALP) and Alizarin Red S staining, which are representative methods of analyzing bone differentiation, were performed. As appears in FIG. 8G, the results showed that the KLF10 gene knockout resulted in an about 2-fold decrease in ALP activity and an about 4.5-fold decrease in mineralization. Therefore, it could be understood that KLF10 expression had an influence on IHH expression and played an important role in bone differentiation.

Example 6

Analysis of Cartilage Regeneration Efficacy of Bone Marrow Stem Cells Expressing MiR-892b The present inventors examined, in a rat cartilage defect model, the cartilage regeneration efficacy of human bone marrow stem cells expressing miR-892b. First, bone marrow stem cells were infected with each of a lentivirus (Lenticontrol) and a miR-892b lentivirus (Lenti-miR-892b) prior to transplanting into a rat cartilage defect model, the cells were secondarily stained (CellVue labeled) using CellVue (Sigma-Aldrich Co. LLC.), which is a far-red fluorescent dye expressing Cy5.5 fluorescence, to examine the distribution of transplanted cells within a living body, and the same were analyzed with an IVIS Lumina II fluorescence analyzing device (see FIG. 9A). Next, to prepare a rat cartilage defect model, a 2×2 mm defect was made in a trochlear groove of femur of an athymic nude rat (NIH Nude; NTac:NIH-Whn; Taconic Biosciences, Inc.), $5\times10^5$ aforementioned lentivirus or miR-892b lentivirus cells suspended in heparin-conjugated fibrin (HCF) were transplanted into the defect, the defect was closed after solidifying a gel, and the regeneration status of each cartilage was observed 6 weeks later. In this case, to help the cartilage differentiation in each transplanted cell, HCF fused with TGF-β3 (50 ng/10 μl HCF) and HCF not fused with TGF-β3 were separately tested. The experimental group was divided into 5 groups, each of which contained 5 rats: Group 1, a negative control group not treated with anything; Group 2, a control group treated with only TGF-β3; Group 3, treated with control-group lentivirus-infected cells; Group 4, treated with control-group lentivirus-infected cells +TGF-β3; Group 5, treated with miR-892b lentivirus-infected cells +TGF-β3. 6 weeks after the surgery, each experimental group was sacrificed, the femur was separated therefrom, and Cy5.5 fluorescent images thereof were analyzed with an IVIS Lumina II fluorescence analyzing device. As appears in FIG. 9B, the results of comparing their relative quantity showed that fluorescence signals were detected only in the cartilage regeneration areas of Groups 3, 4, and 5 (Gr3, Gr4, and Gr5) which had undergone cell transplantation and that the fluorescence intensity of Groups 4 and 5 was about 4 times higher than that of Group 3. Also, the physical properties of regenerated cartilages of each group were evaluated visually by the ICRS macroscopic scoring method, where a higher score indicates that the conditions of regenerated cartilage are excellent. As appears in FIG. 9C, the most excellent conditions were observed from the regenerated cartilages in Groups 4 and 5, which was a result in agreement with the analyzed results of each cartilage tissue. The analysis of a cartilage tissue was carried out by recovering each cartilage tissue from a 14% EDTA solution, cutting the tissue into a thickness of 10 μm by freezing, performing Safranin-O staining on the tissue, and quantifying the same through the Wakitani histological scoring analysis. Unlike in the ICRS macroscopic scoring method, a lower score obtained from the Wakitani histological scoring analysis method indicates a high degree of cartilage regeneration. As shown in FIGS. 9D and 9E, it was found that Groups 4 and 5 exhibited highly excellent cartilage regeneration.

The above description of the invention is only exemplary, and it will be understood by those skilled in the art that various modifications can be made without departing from the scope of the present invention and without changing essential features. Therefore, the above-described examples should be considered in a descriptive sense only and not for the purposes of limitation.

INDUSTRIAL APPLICABILITY

The present invention has an advantage of enabling the use of bone marrow stem cells, which express a composition comprising a Krueppel-like factor 10 (KLF10) gene expression inhibitor, as a chondrocyte therapeutic agent.

We claim:

1. A method of promoting a differentiation of a bone marrow stem cell into a chondrocyte comprising:

expressing a Krueppel-like factor 10 (KLF10) gene expression inhibitor in the bone marrow stem cell.

2. The method of claim 1, wherein the Krueppel-like factor 10 (KLF10) gene consists of a base sequence encoding an amino acid sequence represented by SEQ ID NO. 1.

3. The method of claim 1, wherein the Krueppel-like factor 10 (KLF10) gene expression inhibitor is selected from the group consisting of microRNA (miRNA), small interfering RNA (siRNA), and short hairpin RNA (shRNA), which complementarily bind to mRNA of the Krueppel-like factor 10 (KLF10) gene.

4. The method of claim 3, wherein the microRNA (miRNA) is a miR-892b gene consisting of a base sequence of SEQ ID NO. 4.

5. The method of claim 3, wherein the short hairpin RNA (shRNA) consisting of a base sequence of SEQ ID NO. 2 or 3.

6. The method of claim 3, wherein the Krueppel-like factor 10 (KLF10) gene expression inhibitor is one that has been inserted into an expression vector.

7. The method of claim 1, wherein the composition inhibits chondrocyte hypertrophy and dedifferentiation.

8. A method of treating a cartilage disease comprising:
administering a KLF10 gene expression inhibitor to a subject.

9. The method of claim 8, wherein the KLF10 gene consists of a base sequence encoding an amino acid sequence represented by SEQ ID NO. 1.

10. The method of claim 8, wherein the KLF10 gene expression inhibitor is selected from the group consisting of miRNA, siRNA, and shRNA, which complementarily bind to mRNA of the KLF10 gene.

11. The method of claim 10, wherein the miRNA is a miR-892b gene consisting of a base sequence of SEQ ID NO. 4.

12. The method of claim 10, wherein the shRNA consists of a base sequence of SEQ ID NO. 2 or 3.

13. The method of claim 10, wherein the Krueppel-like factor 10 (KLF10) gene expression inhibitor is inserted into an expression vector.

14. The method of claim 8, wherein the cartilage disease is a disease selected from the group consisting of degenerative arthritis, rheumatoid arthritis, a fracture, damaged muscle tissue, plantar fasciitis, lateral epicondylitis, calcific tendinitis, fracture nonunion, and a damaged joint due to trauma.

* * * * *

SEQUENCE LISTING

```
<160> NUMBER OF SEQ ID NOS: 46

<210> SEQ ID NO 1
<211> LENGTH: 480
<212> TYPE: PRT
<213> ORGANISM: Homo sapiens

<400> SEQUENCE: 1

Met Leu Asn Phe Gly Ala Ser Leu Gln Gln Thr Ala Glu Glu Arg Met
1               5                   10                  15

Glu Met Ile Ser Glu Arg Pro Lys Glu Ser Met Tyr Ser Trp Asn Lys
            20                  25                  30

Thr Ala Glu Lys Ser Asp Phe Glu Ala Val Glu Ala Leu Met Ser Met
        35                  40                  45

Ser Cys Ser Trp Lys Ser Asp Phe Lys Lys Tyr Val Glu Asn Arg Pro
    50                  55                  60

Val Thr Pro Val Ser Asp Leu Ser Glu Glu Glu Asn Leu Leu Pro Gly
65                  70                  75                  80

Thr Pro Asp Phe His Thr Ile Pro Ala Phe Cys Leu Thr Pro Pro Tyr
                85                  90                  95

Ser Pro Ser Asp Phe Glu Pro Ser Gln Val Ser Asn Leu Met Ala Pro
            100                 105                 110

Ala Pro Ser Thr Val His Phe Lys Ser Leu Ser Asp Thr Ala Lys Pro
        115                 120                 125

His Ile Ala Ala Pro Phe Lys Glu Glu Glu Lys Ser Pro Val Ser Ala
    130                 135                 140

Pro Lys Leu Pro Lys Ala Gln Ala Thr Ser Val Ile Arg His Thr Ala
145                 150                 155                 160

Asp Ala Gln Leu Cys Asn His Gln Thr Cys Pro Met Lys Ala Ala Ser
                165                 170                 175

Ile Leu Asn Tyr Gln Asn Asn Ser Phe Arg Arg Arg Thr His Leu Asn
            180                 185                 190

Val Glu Ala Ala Arg Lys Asn Ile Pro Cys Ala Ala Val Ser Pro Asn
        195                 200                 205

Arg Ser Lys Cys Glu Arg Asn Thr Val Ala Asp Val Asp Glu Lys Ala
    210                 215                 220

Ser Ala Ala Leu Tyr Asp Phe Ser Val Pro Ser Ser Glu Thr Val Ile
225                 230                 235                 240

Cys Arg Ser Gln Pro Ala Pro Val Ser Pro Gln Gln Lys Ser Val Leu
                245                 250                 255

Val Ser Pro Pro Ala Val Ser Ala Gly Gly Val Pro Pro Met Pro Val
            260                 265                 270

Ile Cys Gln Met Val Pro Leu Pro Ala Asn Asn Pro Val Val Thr Thr
        275                 280                 285

Val Val Pro Ser Thr Pro Pro Ser Gln Pro Pro Ala Val Cys Pro Pro
    290                 295                 300

Val Val Phe Met Gly Thr Gln Val Pro Lys Gly Ala Val Met Phe Val
305                 310                 315                 320
```

```
Val Pro Gln Pro Val Val Gln Ser Ser Lys Pro Pro Val Val Ser Pro
            325                 330                 335

Asn Gly Thr Arg Leu Ser Pro Ile Ala Pro Ala Pro Gly Phe Ser Pro
            340                 345                 350

Ser Ala Ala Lys Val Thr Pro Gln Ile Asp Ser Ser Arg Ile Arg Ser
        355                 360                 365

His Ile Cys Ser His Pro Gly Cys Gly Lys Thr Tyr Phe Lys Ser Ser
    370                 375                 380

His Leu Lys Ala His Thr Arg Thr His Thr Gly Glu Lys Pro Phe Ser
385                 390                 395                 400

Cys Ser Trp Lys Gly Cys Glu Arg Arg Phe Ala Arg Ser Asp Glu Leu
                405                 410                 415

Ser Arg His Arg Arg Thr His Thr Gly Glu Lys Lys Phe Ala Cys Pro
            420                 425                 430

Met Cys Asp Arg Arg Phe Met Arg Ser Asp His Leu Thr Lys His Ala
        435                 440                 445

Arg Arg His Leu Ser Ala Lys Lys Leu Pro Asn Trp Gln Met Glu Val
    450                 455                 460

Ser Lys Leu Asn Asp Ile Ala Leu Pro Pro Thr Pro Ala Pro Thr Gln
465                 470                 475                 480


<210> SEQ ID NO 2
<211> LENGTH: 48
<212> TYPE: DNA
<213> ORGANISM: Artificial Sequence
<220> FEATURE:
<223> OTHER INFORMATION: shRNA-KLF10-C1

<400> SEQUENCE: 2

gagtatgtat tcctggaaca actcgagttg ttccaggaat acatactc                  48


<210> SEQ ID NO 3
<211> LENGTH: 48
<212> TYPE: DNA
<213> ORGANISM: Artificial Sequence
<220> FEATURE:
<223> OTHER INFORMATION: shRNA-KLF10-C2

<400> SEQUENCE: 3

gaaccctctc aagtgtcaaa tctcgagatt tgacacttga gagggttc                  48


<210> SEQ ID NO 4
<211> LENGTH: 22
<212> TYPE: RNA
<213> ORGANISM: Homo sapiens

<400> SEQUENCE: 4

cacuggcucc uuucugggua ga                                              22


<210> SEQ ID NO 5
<211> LENGTH: 23
<212> TYPE: RNA
<213> ORGANISM: Homo sapiens

<400> SEQUENCE: 5

gcagaucagg acuguaacuc acc                                             23


<210> SEQ ID NO 6
<211> LENGTH: 21
<212> TYPE: RNA
```

<213> ORGANISM: Homo sapiens

<400> SEQUENCE: 6
uggacugccc ugaucuggag a 21

<210> SEQ ID NO 7
<211> LENGTH: 22
<212> TYPE: RNA
<213> ORGANISM: Homo sapiens

<400> SEQUENCE: 7
uuuucaacuc uaaugggaga ga 22

<210> SEQ ID NO 8
<211> LENGTH: 21
<212> TYPE: RNA
<213> ORGANISM: Homo sapiens

<400> SEQUENCE: 8
uccucuucuc ccuccuccca g 21

<210> SEQ ID NO 9
<211> LENGTH: 22
<212> TYPE: DNA
<213> ORGANISM: Artificial Sequence
<220> FEATURE:
<223> OTHER INFORMATION: miR-892b_F

<400> SEQUENCE: 9
cactggctcc tttctgggta ga 22

<210> SEQ ID NO 10
<211> LENGTH: 24
<212> TYPE: DNA
<213> ORGANISM: Artificial Sequence
<220> FEATURE:
<223> OTHER INFORMATION: 5s rRNA_F

<400> SEQUENCE: 10
gatggggcgc gttcagggtg gtat 24

<210> SEQ ID NO 11
<211> LENGTH: 20
<212> TYPE: DNA
<213> ORGANISM: Artificial Sequence
<220> FEATURE:
<223> OTHER INFORMATION: Klf10_F

<400> SEQUENCE: 11
aaagttccca tctgaaggcc 20

<210> SEQ ID NO 12
<211> LENGTH: 21
<212> TYPE: DNA
<213> ORGANISM: Artificial Sequence
<220> FEATURE:
<223> OTHER INFORMATION: Klf10_R

<400> SEQUENCE: 12
tcacaacctt tccagctaca g 21

<210> SEQ ID NO 13
<211> LENGTH: 19
<212> TYPE: DNA
<213> ORGANISM: Artificial Sequence
<220> FEATURE:
<223> OTHER INFORMATION: Ihh_F

<400> SEQUENCE: 13
atgaaggcaa gatcgctcg 19

<210> SEQ ID NO 14
<211> LENGTH: 19
<212> TYPE: DNA
<213> ORGANISM: Artificial Sequence
<220> FEATURE:
<223> OTHER INFORMATION: Ihh_R

<400> SEQUENCE: 14
gatagccagc gagttcagg 19

<210> SEQ ID NO 15
<211> LENGTH: 20
<212> TYPE: DNA
<213> ORGANISM: Artificial Sequence
<220> FEATURE:
<223> OTHER INFORMATION: Ptch1_F

<400> SEQUENCE: 15
tcttggtgtt ggtgtggatg 20

<210> SEQ ID NO 16
<211> LENGTH: 19
<212> TYPE: DNA
<213> ORGANISM: Artificial Sequence
<220> FEATURE:
<223> OTHER INFORMATION: Ptch1_R

<400> SEQUENCE: 16
attgctgatg gacgtgagg 19

<210> SEQ ID NO 17
<211> LENGTH: 20
<212> TYPE: DNA
<213> ORGANISM: Artificial Sequence
<220> FEATURE:
<223> OTHER INFORMATION: Ptch2_F

<400> SEQUENCE: 17
tgctctttct gggactgttg 20

<210> SEQ ID NO 18
<211> LENGTH: 21
<212> TYPE: DNA
<213> ORGANISM: Artificial Sequence
<220> FEATURE:
<223> OTHER INFORMATION: Ptch2_R

<400> SEQUENCE: 18
agcttctcct tggtgtaatg c 21

<210> SEQ ID NO 19
<211> LENGTH: 22
<212> TYPE: DNA
<213> ORGANISM: Artificial Sequence
<220> FEATURE:
<223> OTHER INFORMATION: Smo_F

<400> SEQUENCE: 19
gaagatcaac ctgtttgcca tg 22

```
<210> SEQ ID NO 20
<211> LENGTH: 20
<212> TYPE: DNA
<213> ORGANISM: Artificial Sequence
<220> FEATURE:
<223> OTHER INFORMATION: Smo_R

<400> SEQUENCE: 20

tttggctcat cgtcactctg                                                  20


<210> SEQ ID NO 21
<211> LENGTH: 20
<212> TYPE: DNA
<213> ORGANISM: Artificial Sequence
<220> FEATURE:
<223> OTHER INFORMATION: Gli-2_F

<400> SEQUENCE: 21

gtcagccttt ggacacacac                                                  20


<210> SEQ ID NO 22
<211> LENGTH: 20
<212> TYPE: DNA
<213> ORGANISM: Artificial Sequence
<220> FEATURE:
<223> OTHER INFORMATION: Gli-2_R

<400> SEQUENCE: 22

tctgcttgtt ctggttggtg                                                  20


<210> SEQ ID NO 23
<211> LENGTH: 21
<212> TYPE: DNA
<213> ORGANISM: Artificial Sequence
<220> FEATURE:
<223> OTHER INFORMATION: Wnt3a_F

<400> SEQUENCE: 23

atcaagattg gcatccagga g                                                21


<210> SEQ ID NO 24
<211> LENGTH: 18
<212> TYPE: DNA
<213> ORGANISM: Artificial Sequence
<220> FEATURE:
<223> OTHER INFORMATION: Wnt3a_R

<400> SEQUENCE: 24

caatggcgtg gacaaagg                                                    18


<210> SEQ ID NO 25
<211> LENGTH: 20
<212> TYPE: DNA
<213> ORGANISM: Artificial Sequence
<220> FEATURE:
<223> OTHER INFORMATION: Wnt7a_F

<400> SEQUENCE: 25

gggactatga accggaaagc                                                  20


<210> SEQ ID NO 26
<211> LENGTH: 20
<212> TYPE: DNA
<213> ORGANISM: Artificial Sequence
<220> FEATURE:
<223> OTHER INFORMATION: Wnt7a_R
```

<400> SEQUENCE: 26
ggcctgggat cttgttacag 20

<210> SEQ ID NO 27
<211> LENGTH: 20
<212> TYPE: DNA
<213> ORGANISM: Artificial Sequence
<220> FEATURE:
<223> OTHER INFORMATION: Wnt6_F

<400> SEQUENCE: 27
gagagtgcca gttccagttc 20

<210> SEQ ID NO 28
<211> LENGTH: 18
<212> TYPE: DNA
<213> ORGANISM: Artificial Sequence
<220> FEATURE:
<223> OTHER INFORMATION: Wnt6_R

<400> SEQUENCE: 28
tgatggcgaa cacgaagg 18

<210> SEQ ID NO 29
<211> LENGTH: 19
<212> TYPE: DNA
<213> ORGANISM: Artificial Sequence
<220> FEATURE:
<223> OTHER INFORMATION: Wnt9b_F

<400> SEQUENCE: 29
agtgccagtt tcagttccg 19

<210> SEQ ID NO 30
<211> LENGTH: 21
<212> TYPE: DNA
<213> ORGANISM: Artificial Sequence
<220> FEATURE:
<223> OTHER INFORMATION: Wnt9b_R

<400> SEQUENCE: 30
ggaaagctgt ctctttgaag c 21

<210> SEQ ID NO 31
<211> LENGTH: 20
<212> TYPE: DNA
<213> ORGANISM: Artificial Sequence
<220> FEATURE:
<223> OTHER INFORMATION: Ctnnb1_F

<400> SEQUENCE: 31
gttcagttgc ttgttcgtgc 20

<210> SEQ ID NO 32
<211> LENGTH: 21
<212> TYPE: DNA
<213> ORGANISM: Artificial Sequence
<220> FEATURE:
<223> OTHER INFORMATION: Ctnnb1_R

<400> SEQUENCE: 32
gttgtgaaca tcccgagcta g 21

<210> SEQ ID NO 33

```
<211> LENGTH: 20
<212> TYPE: DNA
<213> ORGANISM: Artificial Sequence
<220> FEATURE:
<223> OTHER INFORMATION: Runx2_F

<400> SEQUENCE: 33

ttacttacac cccgccagtc                                                  20


<210> SEQ ID NO 34
<211> LENGTH: 20
<212> TYPE: DNA
<213> ORGANISM: Artificial Sequence
<220> FEATURE:
<223> OTHER INFORMATION: Runx2_R

<400> SEQUENCE: 34

tatggagtgc tgctggtctg                                                  20


<210> SEQ ID NO 35
<211> LENGTH: 20
<212> TYPE: DNA
<213> ORGANISM: Artificial Sequence
<220> FEATURE:
<223> OTHER INFORMATION: Alpl_F

<400> SEQUENCE: 35

gacaagaagc ccttcactgc                                                  20


<210> SEQ ID NO 36
<211> LENGTH: 20
<212> TYPE: DNA
<213> ORGANISM: Artificial Sequence
<220> FEATURE:
<223> OTHER INFORMATION: Alpl_R

<400> SEQUENCE: 36

agactgcgcc tggtagttgt                                                  20


<210> SEQ ID NO 37
<211> LENGTH: 21
<212> TYPE: DNA
<213> ORGANISM: Artificial Sequence
<220> FEATURE:
<223> OTHER INFORMATION: GAPDH_F

<400> SEQUENCE: 37

cacatggcct ccaaggagta a                                                21


<210> SEQ ID NO 38
<211> LENGTH: 21
<212> TYPE: DNA
<213> ORGANISM: Artificial Sequence
<220> FEATURE:
<223> OTHER INFORMATION: GAPDH_R

<400> SEQUENCE: 38

gtacatgaca aggtgcggct c                                                21


<210> SEQ ID NO 39
<211> LENGTH: 1443
<212> TYPE: DNA
<213> ORGANISM: Homo sapiens

<400> SEQUENCE: 39

atgctcaact tcggtgcctc tctccagcag actgcggagg aaagaatgga aatgatttct      60
```

```
gaaaggccaa aagagagtat gtattcctgg aacaaaactg cagagaaaag tgattttgaa    120

gctgtagaag cacttatgtc aatgagctgc agttggaagt ctgattttaa gaaatacgtt    180

gaaaacagac ctgttacacc agtatctgat ttgtcagagg aagagaatct gcttccggga    240

acacctgatt ttcatacaat cccagcattt tgtttgactc caccttacag tccttctgac    300

tttgaaccct ctcaagtgtc aaatctgatg gcaccagcgc catctactgt acacttcaag    360

tcactctcag atactgccaa acctcacatt gccgcacctt tcaaagagga agaaaagagc    420

ccagtatctg cccccaaact ccccaaagct caggcaacaa gtgtgattcg tcatacagct    480

gatgcccagc tatgtaacca ccagacctgc ccaatgaaag cagccagcat cctcaactat    540

cagaacaatt cttttagaag aagaacccac ctaaatgttg aggctgcaag aaagaacata    600

ccatgtgccg ctgtgtcacc aaacagatcc aaatgtgaga gaaacacagt ggcagatgtt    660

gatgagaaag caagtgctgc actttatgac ttttctgtgc cttcctcaga gacggtcatc    720

tgcaggtctc agccagcccc tgtgtcccca caacagaagt cagtgttggt ctctccacct    780

gcagtatctg caggggggagt gccacctatg ccggtcatct gccagatggt tccccttcct    840

gccaacaacc ctgttgtgac aacagtcgtt cccagcactc ctcccagcca gccaccagcc    900

gtttgccccc ctgttgtgtt catgggcaca caagtcccca aaggcgctgt catgtttgtg    960

gtaccccagc ccgttgtgca gagttcaaag cctccggtgg tgagcccgaa tggcaccaga   1020

ctctctccca ttgcccctgc tcctgggttt tccccttcag cagcaaaagt cactcctcag   1080

attgattcat caaggataag gagtcacatc tgtagccacc caggatgtgg caagacatac   1140

tttaaaagtt cccatctgaa ggcccacacg aggacgcaca caggagaaaa gcctttcagc   1200

tgtagctgga aaggttgtga aaggaggttt gcccgttctg atgaactgtc cagacacagg   1260

cgaacccaca cgggtgagaa gaaatttgcg tgccccatgt gtgaccggcg gttcatgagg   1320

agtgaccatt tgaccaagca tgcccggcgc catctatcag ccaagaagct accaaactgg   1380

cagatggaag tgagcaagct aaatgacatt gctctacctc caacccctgc tcccacacag   1440

tga                                                                  1443
```

<210> SEQ ID NO 40
<211> LENGTH: 341
<212> TYPE: DNA
<213> ORGANISM: Artificial Sequence
<220> FEATURE:
<223> OTHER INFORMATION: NheI_EcoRI

<400> SEQUENCE: 40

```
tggagagcag tgggatgagc attctctagg acttatgaat caaattgttc aggcatcatg     60

ttctattgag gggaatgata aaacctgcag gggacaatgg tggggcacag ggcagcgctt    120

ccgcaatcag ccatgctgtg tgcaatgccc tactcagaaa ggtgccattt atgtagattt    180

tatgtcactg gctcctttct gggtagagca aggctcacca tgtatatatt tgtggtggcc    240

tttgtacccg tgttggagta gagctgcaaa agcctcaagc tgccttccct gataacagga    300

gaacctagct ggccatgtgg acctcaggca tcctcaagat g                        341
```

<210> SEQ ID NO 41
<211> LENGTH: 22
<212> TYPE: DNA
<213> ORGANISM: Artificial Sequence
<220> FEATURE:
<223> OTHER INFORMATION: KLF10 3'UTR -continued

```
<400> SEQUENCE: 41

ttggtctcag cgggagccag tg                                          22


<210> SEQ ID NO 42
<211> LENGTH: 22
<212> TYPE: DNA
<213> ORGANISM: Artificial Sequence
<220> FEATURE:
<223> OTHER INFORMATION: WNT6 3'UTR

<400> SEQUENCE: 42

ttagactgga aaaaagccag tc                                          22


<210> SEQ ID NO 43
<211> LENGTH: 22
<212> TYPE: DNA
<213> ORGANISM: Artificial Sequence
<220> FEATURE:
<223> OTHER INFORMATION: KLF10-3'UTR-MUT

<400> SEQUENCE: 43

ttggtctcag cgggaattca tg                                          22


<210> SEQ ID NO 44
<211> LENGTH: 22
<212> TYPE: DNA
<213> ORGANISM: Artificial Sequence
<220> FEATURE:
<223> OTHER INFORMATION: WNT6-3'UTR-MUT

<400> SEQUENCE: 44

ttagactgga aaaaaattca tc                                          22


<210> SEQ ID NO 45
<211> LENGTH: 58
<212> TYPE: DNA
<213> ORGANISM: Artificial Sequence
<220> FEATURE:
<223> OTHER INFORMATION: shRNA-KLF10-C1

<400> SEQUENCE: 45

aattcaaaaa gagtatgtat tcctggaaca actcgagttg ttccaggaat acatactc       58


<210> SEQ ID NO 46
<211> LENGTH: 58
<212> TYPE: DNA
<213> ORGANISM: Artificial Sequence
<220> FEATURE:
<223> OTHER INFORMATION: shRNA-KLF10-C2

<400> SEQUENCE: 46

aattcaaaaa gaaccctctc aagtgtcaaa tctcgagatt tgacacttga gagggttc       58
```